(12) United States Patent
Leuchs et al.

(10) Patent No.: US 10,266,810 B2
(45) Date of Patent: Apr. 23, 2019

(54) METHOD FOR LARGE SCALE PRODUCTION AND PURIFICATION OF PARVOVIRUS

(71) Applicant: Deutsches Krebsforschungszentrum, Heidelberg (DE)

(72) Inventors: Barbara Leuchs, Heidelberg (DE); Mandy Roscher, Schriesheim (DE); Marcus Müller, Bad Rappenau (DE); Jean Rommelaere, Heidelberg (DE)

(73) Assignee: Deutsches Krebsforschungszentrum, Heidelberg (DE)

( * ) Notice: Subject to any disclaimer, the term of this patent is extended or adjusted under 35 U.S.C. 154(b) by 0 days.

(21) Appl. No.: 15/739,684

(22) PCT Filed: Jun. 22, 2016

(86) PCT No.: PCT/EP2016/001066
§ 371 (c)(1),
(2) Date: Dec. 22, 2017

(87) PCT Pub. No.: WO2016/206807
PCT Pub. Date: Dec. 29, 2016

(65) Prior Publication Data
US 2018/0187166 A1    Jul. 5, 2018

(30) Foreign Application Priority Data
Jun. 23, 2015 (EP) .................... 15173385

(51) Int. Cl.
| | |
|---|---|
| C12N 7/00 | (2006.01) |
| C12N 7/02 | (2006.01) |
| G01N 33/569 | (2006.01) |
| C07K 16/08 | (2006.01) |

(52) U.S. Cl.
CPC ............... *C12N 7/02* (2013.01); *C12N 7/00* (2013.01); *G01N 33/56983* (2013.01); *C07K 16/081* (2013.01); *C12N 2750/14323* (2013.01); *C12N 2750/14351* (2013.01); *C12N 2750/14361* (2013.01)

(58) Field of Classification Search
None
See application file for complete search history.

(56) References Cited

U.S. PATENT DOCUMENTS 8,828,400 B2 *    9/2014    Leuchs ................ C07K 16/081
                                                         424/159.1

OTHER PUBLICATIONS

Leuchs et al. A novel scalable, robust downstream process for oncolytic rat parvovirus: isoelectric point-based elimination of empty particles.Appl Microbiol Biotechnol. Apr. 2017;101(8):3143-3152 (Year: 2017).*
Bhat et al. NK-cell-dependent killing of colon carcinoma cells is mediated by natural cytotoxicity receptors (NCRs) and stimulated by parvovirus infection of target cells. BMC Cancer. Jul. 31, 2013;13:367. (Year: 2013).*
Halder et al. Production, purification, crystallization and structure determination of H-1 Parvovirus. Acta Crystallogr Sect F Struct Biol Cryst Commun. Dec. 1, 2012;68(Pt 12):1571-6. (Year: 2012).*

* cited by examiner

*Primary Examiner* — Michelle S Horning
(74) *Attorney, Agent, or Firm* — Leason Ellis LLP

(57) ABSTRACT

Described is a reproducible, effective and scalable process for parvovirus production including characterization strategies, preferably production of H-1PV.

9 Claims, 11 Drawing Sheets

METHOD FOR LARGE SCALE PRODUCTION AND PURIFICATION OF PARVOVIRUS

CROSS REFERENCE TO RELATED APPLICATIONS

This application is a 371 national phase of International Application No. PCT/EP2016/001066 filed Jun. 22, 2016, which claims priority to EP Application No. 15173385.4 filed Jun. 23, 2015. The entire contents of these applications are hereby incorporated herein by reference.

The present invention provides a reproducible, effective and scalable process for parvovirus production, preferably for the production of H-1PV, as well as a process for purification of (infectious) parvovirus particles.

H-1PV belongs to the genus *Protoparvovirus* within the Parvovirinae subfamily of Parvoviridae (Cotmore et al., 2014). It consists of a non-enveloped icosahedral capsid 25 nm in diameter and contains a single-stranded DNA genome about 5 kb long, encoding non-structural proteins—notably NS1 (83 kDa) and NS2 (25 kDa)—and the capsid proteins VP1 (81 kDa) and VP2 (65 kDa). Another capsid protein, VP3 (63 kDa), is generated by post-translational cleavage of VP2 (Faisst et al., 1995; Halder et al., 2012; Hanson and Rhode, 1991; Toolan et al., 1960). Protoparvoviruses replicate in a S-phase-dependent fashion and undergo a lytic cycle after infection of permissive cells (Burnett et al., 2006). While the natural host of H-1PV is the rat, this virus has recently raised much interest because it replicates preferentially in transformed cells, including a number of human tumor cells. The virus thus has oncolytic and oncosuppressive properties that have been demonstrated in various cell cultures and animal models (Nuesch et al., 2012; Rommelaere et al., 2010). In xenograft models, H-1PV has been shown to suppress a number of human tumors, including cervical tumors (Faisst et al., 1998; Li et al., 2013), pancreatic tumors (Angelova et al., 2009b; Grekova et al., 2011), mammary carcinomas (Dupressoir et al., 1989), gliomas (Geletneky et al., 2010; Kipianova et al., 2011), and lymphomas (Angelova et al., 2009a). In addition, H-1PV has been shown to be successful in eliminating cancer stem cells (EP 2 404 609 A1). On the basis of these preclinical proofs of concept, a first clinical trial (phase I/IIa) of H-1PV was launched in 2011, for patients with recurrent glioblastoma multiforme (Geletneky et al., 2012).

To test and eventually exploit the therapeutic potential of H-1PV, it is necessary to develop an efficient, simple, and reproducible virus production process and reliable assays for the quantitative and qualitative characterization of final virus batches. Methods have been published for small-scale production of H-1PV in NB-324K cells and its purification by cesium chloride (Halder et al., 2012; Paradiso, 1981) or Iodixanol (Wrzesinski et al., 2003; Zolotukhin et al., 1999) density gradient centrifugation. The literature also describes titration of infectious virions by plaque assay (Tattersall and Bratton, 1983) of H-1PV physical particles by electron microscopy (Halder et al., 2012) or hemagglutination assay (Kongsvik and Toolan, 1972) and of genome-containing particles by quantitative PCR (Lacroix et al., 2010). However, no systematic comparative analyses have been conducted to determine and optimize virus yield and purity or the sensitivity of analytical methods for virus quantification and quality monitoring.

Thus, the technical problem underlying the present invention is to standardize and optimize parvovirus production, purification, and characterization.

The solution of said technical problem is achieved by providing the embodiments characterized in the claims.

Oncolytic *protoparvovirus* research has reached the stage of translation into clinical practice, with a first phase I/IIa study of H-1PV in patients with recurrent resectable malignant glioma (Geletneky et al., 2012). This trial is expected to be followed by further clinical studies aiming to assess efficacy and to extend the approach to other cancers such as pancreatic carcinoma or neuroblastoma (Lacroix et al., 2010; Li et al., 2013). These developments rely on the availability of robust procedures for *protoparvovirus* production and characterization. On the one hand, standardized procedures are needed to generate preclinical data that can provide the proof of concept. The use of well-characterized virus preparations and analytical methods is indeed a prerequisite to obtaining valid, reproducible evidence of the therapeutic efficacy of oncolytic protoparvoviruses in oncology. On the other hand, standard operating procedures are also required for the transfer of technologies and standards to the certified facilities in charge of producing clinical batches and establishing their specifications.

During the experiments resulting in the present invention major innovations for large-scale virus production, with elimination of unwanted contaminants through improved virus batch clarification and infectious particle purification were introduced. The inventors focused on developing standardized production, purification, and characterization procedures as a basis for exploiting H-1PV both preclinically and in clinical trials for anticancer virotherapy. Two infection and two virus purification strategies were tested and the resulting virus preparations compared for their purity and full-, infectious-, and empty-particle contents. The adopted production process, which involves culturing and infecting NB-324K human newborn kidney cells transformed with simian virus 40 (SV40) (Tattersall and Bratton, 1983) in a conventional collection system (e.g. 10-layer CellSTACK® (CS) chambers; preferred yield: $1 \times 10^3$ infectious units per infected cell), is simple, scalable, and reproducible. Downstream processing to eliminate contaminating DNA and protein includes DNAse treatment, filtration, and two Iodixanol density-gradient centrifugations, the first gradient being a step gradient and the second, either a step (e.g. titer reached: $1 \times 10^{10}$ PFU/ml) or a continuous gradient (e.g. titer reached: $3 \times 10^{11}$ PFU/ml). A procedure was also developed for obtaining infectious particle-free preparations of empty virions for research purposes: cesium chloride density gradient centrifugation followed by UV irradiation (e.g. titer achieved: $1 \times 10^{14}$ physical particles/ml). For quick, sensitive determination of physical particles (and hence, particle-to-infectivity ratios), a "Capsid-ELISA" was developed, based on a novel monoclonal antibody that specifically targets assembled capsids.

The present invention illustrates this standardization effort. It describes methods to support preclinical research. Improvements at three steps of H-1PV stock preparation were achieved: (1) reproducible, standardized, large-scale virus production, (2) virus purification and concentration by alternative procedures, and (3) implementation of quality control criteria.

(A) Reproducible, Standardized, Large-Scale H-1PV Production

A robust, standardized H-1PV production process was established, as illustrated below for five individual virus batches and as summarized in FIG. 9.

A virus yield of $2 \times 10^{11}$ PFU with a concentration of $1 \times 10^{10}$ PFU/ml, compatible with preclinical and clinical usage, was achieved with a single 10-layer CS chamber. This yield corresponds to a productivity of about $1\times10^3$ infectious particles per infected cell. The 10-layer system provides approximately the same attachment surface as a 100×10 cm cell culture dish (Halder et al., 2012). Efficient production was possible due to the good condition of the producer cells (NB-324K), with a viability over 95%, a passage number below 20, no mycoplasma contamination (Multiplexion, Germany), and the consistent quality of the FBS.

Initial attempts at up-scaling H-1PV production in a roller bottle system failed, even when intermittent 5% $CO_2$ gassing and Hepes/$NaHCO_3$ buffering were applied (data not shown). The inventors, however, achieved optimal intracellular milieu for virus production by $CO_2$ gassing.

A simple and efficient way to achieve up-scaling was to use CS chambers, giving recoveries of up to $1\times10^{12}$ PFU from five 10-layer chambers. Further up-scaling would be possible with 40-layer chambers, although their handling of shaking and gassing is more cumbersome. Further up-scaling with adherent cells would involve the use of carriers, as described for vaccine production (Rajendran et al., 2014). An attractive alternative would be to use suspension cell cultures in wave reactors, as described for mink enteritis PV vaccine production (Hundt et al., 2007). A related method concerning high titer recombinant AAV vector production in adherent and suspension cells is described in WO 2015/031686 A1.

(B) Efficient Purification and Concentration of H-1PV Preparations

Unprocessed virus harvests contained full, empty, and intermediate-density particles, and were contaminated by both viral and host-cell DNA and proteins. They were first DNAse treated and then clarified through a filter (e.g. 0.2 µm filter). This resulted in elimination of 37% of the host-cell DNA and unpackaged viral DNA and of 24% of the total protein. Residual fragments of host-cell DNA proved to be smaller than 62 bp. H-1PV was further purified by Iodixanol or CsCl gradient centrifugation. These methods were compared regarding the H-1PV titer obtained, separation of full from empty particles, and the presence of contaminating proteins, as measured by electron microscopy and Coomassie blue staining after SDS-PAGE. In a recent report (Halder et al., 2012) high purification of empty versus full particles was achieved through three rounds of CsCl centrifugation, as evidenced on electron micrographs. Yet because of CsCl toxicity, this procedure is not recommended for standard purification of preclinical and clinical virus batches. This prompted the inventors to develop a two-step purification procedure involving successive IOD-PBS and VIS-Ringer density gradient centrifugations.

Comparison of CsCl and VIS-Ringer gradient fractions shows the respective pros and cons of these methods. On the one hand, CsCl gradient centrifugation appears as method of choice for preparing empty virions for research purposes, since the particle-to-PFU ratio in the empty-particle fraction was ten times higher after CsCl density gradient centrifugation than after the Vis-Ringer step, with a specific titer exceeding $10^{14}$ PP/mg protein. On the other hand, the two-step Iodixanol gradient centrifugation procedure emerges as a better way to purify infectious particles because of avoiding CsCl toxicity (a disadvantage in the case of clinical applications) and because it is less cost- and time-consuming (half a day versus three days for CsCl centrifugation). Furthermore, it yields specific activity titers around $5\times10^{11}$ PFU/mg protein. The virus concentration in the Vis-Ringer full-particle fraction was about $1\times10^{10}$ PFU/ml, and increased up to $3\times10^{11}$ PFU/ml when the Vis-Ringer step gradient was replaced with a continuous gradient. The virus fractions collected from Vis-Ringer gradients were stable for over two years, allowing these fractions to be used as virus stocks without any further buffer change. For these various reasons, the Iodixanol purification procedure is routinely used to prepare stocks of infectious H-1PV. Besides the density gradient centrifugation methods presented here, other virus purification procedures validated in other systems deserve to be tested for their applicability to the preparation of oncolytic PVs. Chromatography and chromatofocusing are of special interest for large-scale production (Okada et al., 2009), since empty and full particles can be separated by chromatography, as shown for AAV (Qu et al., 2007). The use of membrane absorbers to capture the *protoparvovirus* MVM has also been described recently (Weaver et al., 2013).

(C) High Quality of Full- and Empty-Particle Batches

The International Conference on Harmonization has issued guidelines for this type of product in "Specifications: Test Procedures and Acceptance Criteria for Biotechnological/Biological Products" (Q6B, 1999). These guidelines specify the levels at which drug products must be characterized, including their physicochemical properties, biological activity, immunochemical properties, quantity, purity, impurities, and contaminants. In principle, the source material, purification steps, and formulation ensure the consistent quality of a drug product. H-1PV batches were quantified and specified according to the ICH guidelines. A particular issue addressed in the present invention was the contamination of full-particle virus stocks by empty particles. This is important because empty particles, although non-toxic, may affect cell physiology and induce antiviral immune responses (Gao et al., 2014). Methods are thus required for quantitating both genome-containing virions and total physical viral particles. While quantitative PCR appears as a good way to quantify full virions, there is a need for a more convenient method of physical particle quantification. A "Capsid-ELISA" using the mAb BL-H1 was developed in the present invention which specifically recognizes assembled H-1PV capsids. This ELISA proved to be less cumbersome, more reliable, and also more sensitive than the hemagglutination test classically used to detect parvoviral particles. Clearing empty particles out of full-virion batches remains a goal for the further improvement of purification procedures. Conversely, it is also important to obtain empty-particle stocks that are free of infectious virions and can be studied for their in vitro and in vivo effects in the absence of virus infectivity. This was achieved by irradiating empty-particle batches with UV light to inactivate infectious virions. T procedure results in empty-particle batches containing less than $10^{-10}$% infectious virions.

(D) Application Scope of the BL-H1 Monoclonal Antibody

Besides its use in the qualitative and quantitative control of virus stocks, mAb BL-H1 has proved valuable for both preclinical and clinical-trial-accompanying research. It is used as a standard to quantify H-1PV-specific antibodies in serum from treated animals (Grekova et al., 2011) and could be used in the future to monitor seroconversion in patients. BL-H1 can also be used as capture antibody in an ELISA detecting viremia in infected subjects and to screen rats from animal facilities for PV infection (EP 2 332 986 A1).

Protein extracts prepared from 293T HEK cells transfected with an infectious H-1PV molecular clone were analyzed by sucrose gradient centrifugation. Individual fractions were analyzed for the presence of GP, IU, HAU, and VP proteins. VPs were detected, respectively, by western dot blotting with BL-H1 or aVP antibodies. The data show that BL-H1 mAb specifically recognizes assembled capsids while αVP recognizes VP proteins.

Figure 2:
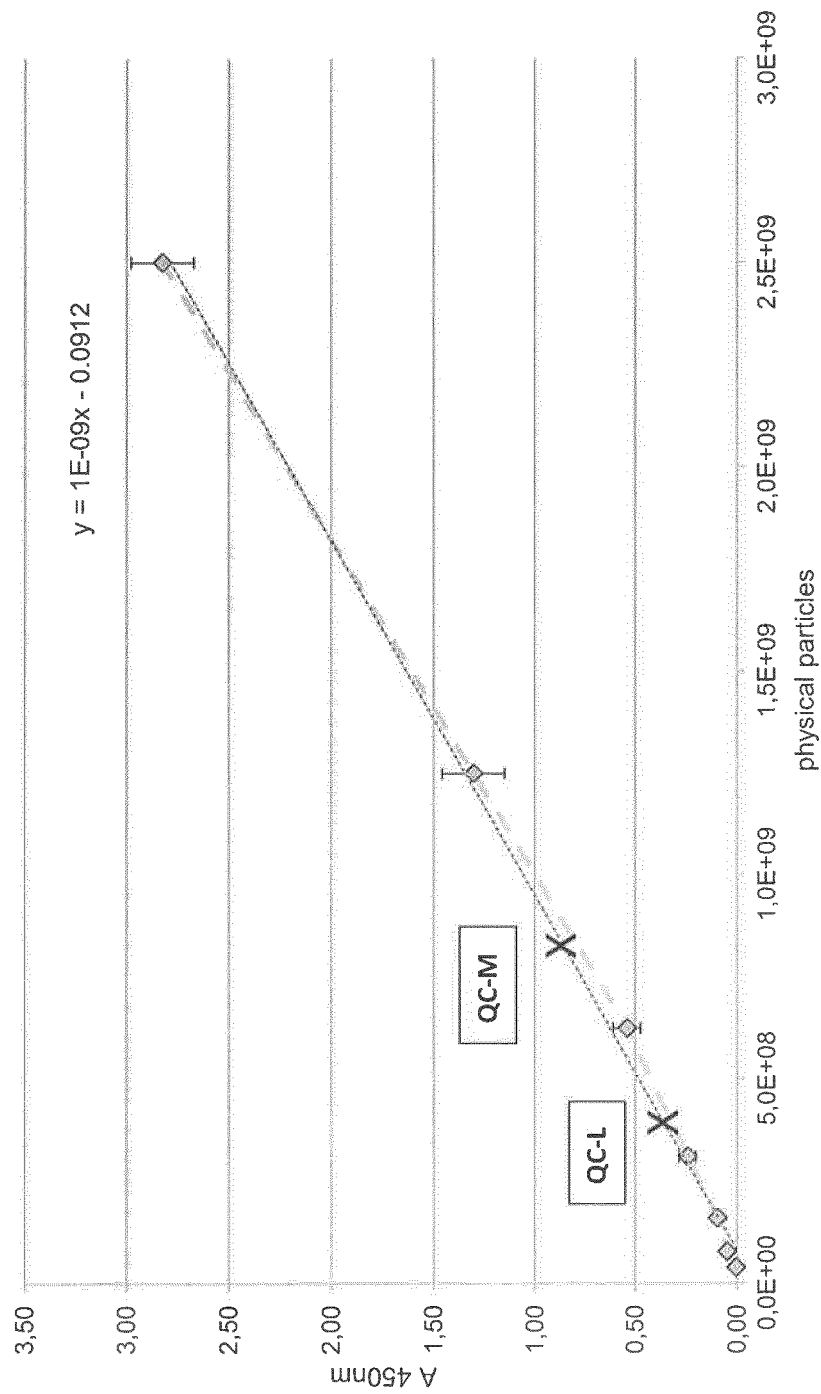

FIG. 2: Characterization of the H-1PV Capsid ELISA

The absorbance at 450 nm is plotted versus the number of H-1PV particles added (as determined by ELMI). The indicated values represent means with standard deviation bars of 3 independent measurements. A linear dose-response was derived from the regression analysis of data. The samples indicated as "QC-L" and QC-M" contained, respectively, 4 and $8 \times 10^8$ particles and were used subsequently as low- and medium-concentration quality control standards.

Figure 3:
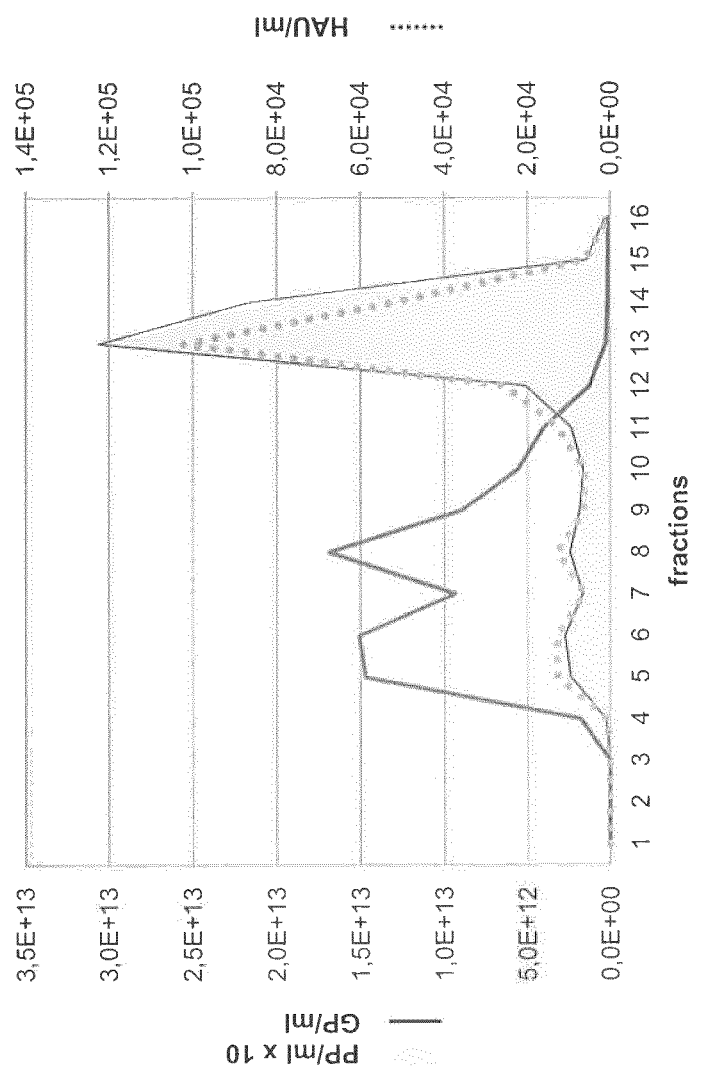

FIG. 3: Separation of empty from full H-1PV capsids by CsCl gradient centrifugation Capsids were detected by either hemagglutination assay (HAU) or Capsid-ELISA (PP) while genome containing viral particles (GP) were quantified by Q-PCR.

Figure 4:
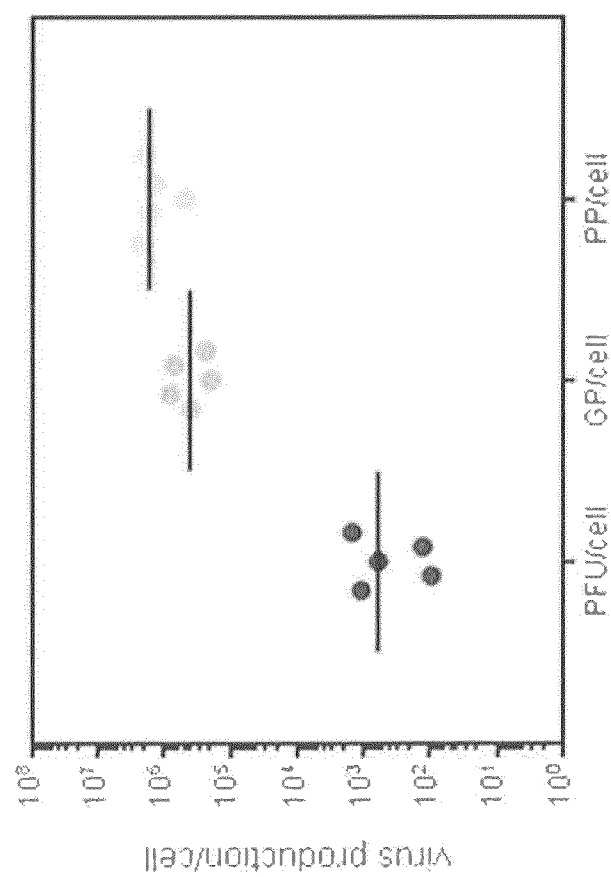

FIG. 4: Reproducibility of H-1PV production

After production in a 10-layer CS, virus harvests were prepared and analyzed. PFU, GP, and PP titers were determined and are expressed relative to the number of cells in the CS at the time of infection. Values for 5 independent productions are shown.

FIG. 5: Extent of full-from empty-particle separation after density gradient centrifugation in either (a) IOD-PBS and VIS-Ringer successively or (b) CsCl The PFU, GP, and PP titers of the indicated fractions are shown (means with standard deviations from 5 independent experiments).

FIG. 6: Recovery, specific activity and particle-to-infectivity ratio in full- and empty-particle fractions Virus harvest was clarified and then purified by IOD-PBS and VIS-Ringer density gradient centrifugation or by CsCl density gradient centrifugation. Samples of clarified harvest, virus-containing IOD-PBS gradient fraction, full- and empty-particle VIS-Ringer gradient fractions, and full- and empty-particle CsCl gradient fractions were analyzed. (a) Specific activity (PFU/mg), PFU recovery (%), and PP/PFU ratio in the intermediate and full-particle fractions. (b) Specific capsid titer (PP/mg), PP recovery (%), and PP/PFU ratio in the intermediate and empty-particle fractions.

Figure 7:
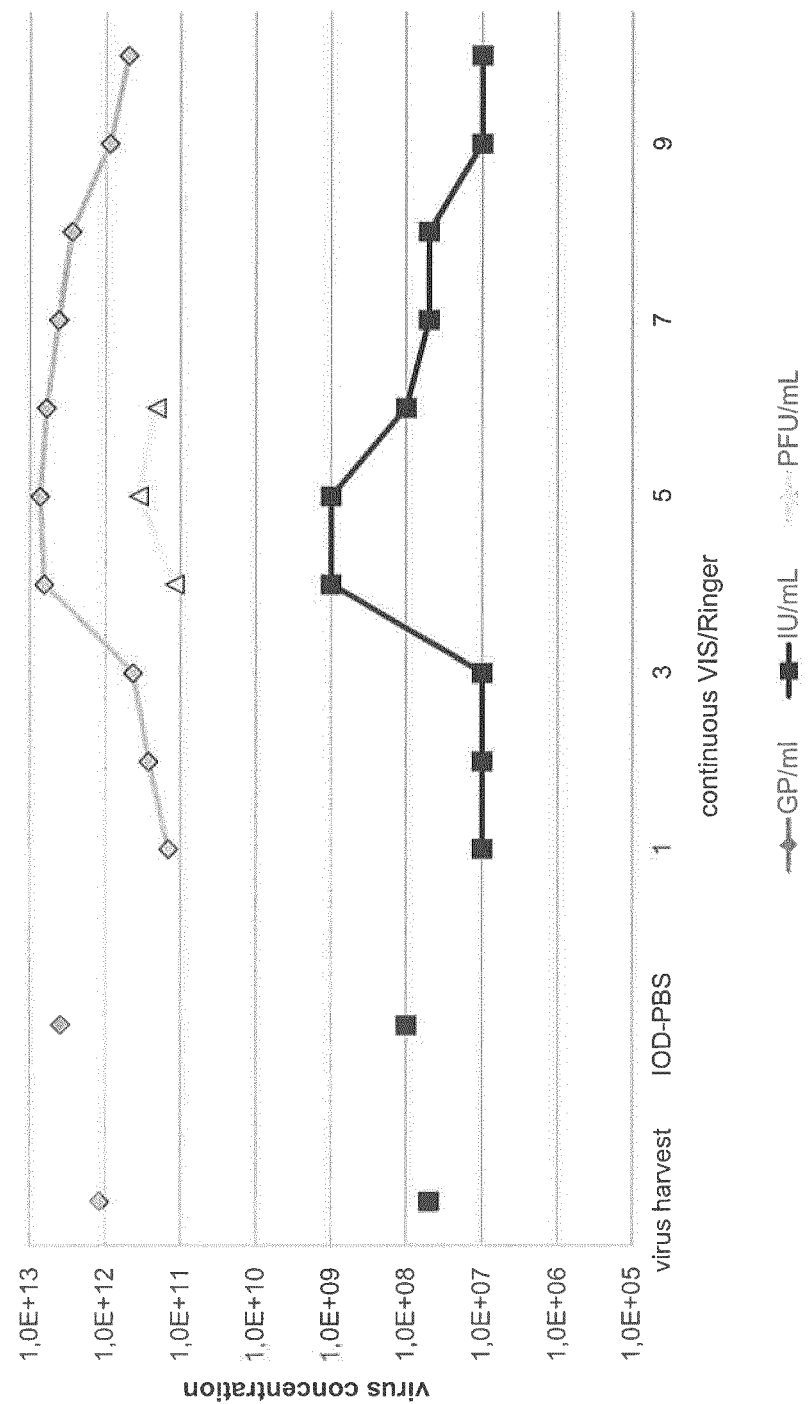

FIG. 7: Concentrating H-1PV by continuous VIS-Ringer gradient centrifugation

An H-1PV harvest was clarified and then purified by density gradient centrifugation, first in an IOD-PBS step gradient and then in a VIS-Ringer continuous gradient. GP and IU titers were determined in the clarified virus harvest, after the IOD-PBS step gradient, and in fractions 1-10 of the continuous gradient. The IU-rich fractions 4-6 were further analyzed, showing infectious H-1PV concentrations up to $3.0 \times 10^{11}$ PFU/ml.

Figure 8:
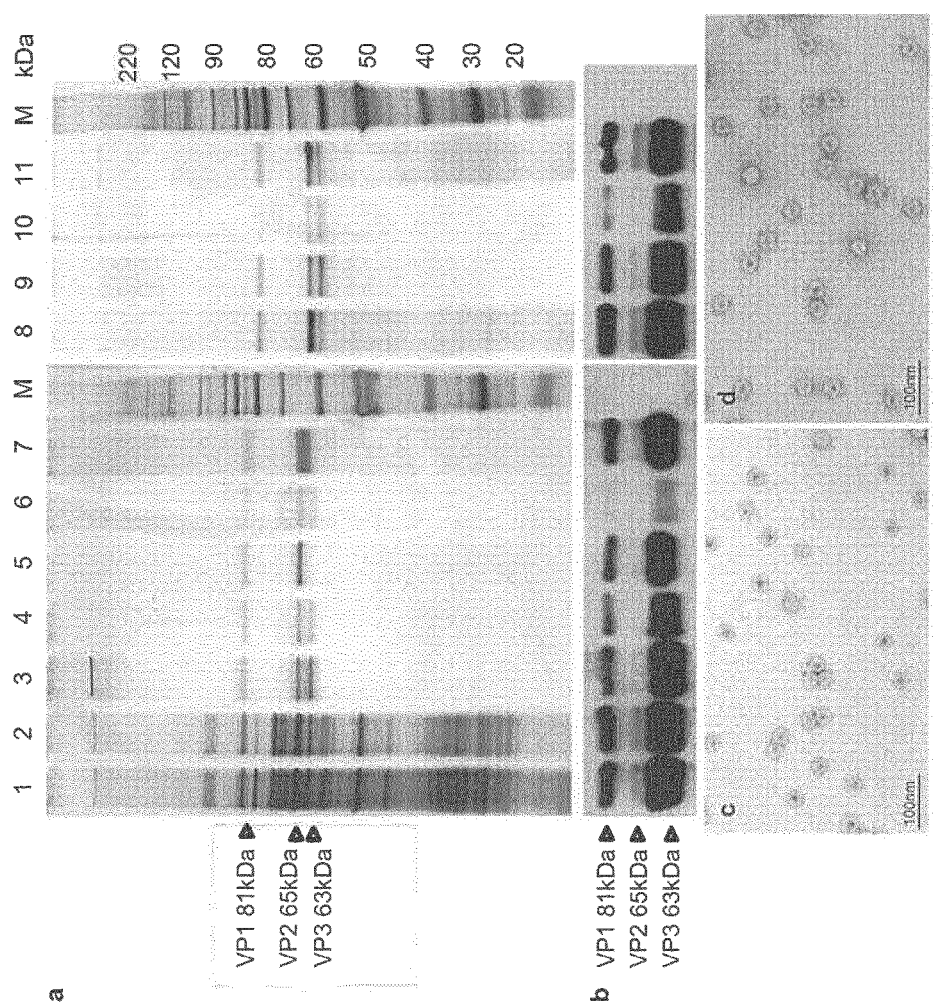

FIG. 8: Protein composition of virus batches from successive purification steps

Panels a,b: Protein extracts from virus samples ($1 \times 10^{10}$ PP) were analyzed by SDS-PAGE and revealed by (a) silver staining or (b) immunoblotting with αVP antibodies.

Lane 1: Virus harvest, lane 2: clarified virus harvest, lanes 3-7: CsCl gradient fractions corresponding to full (3), intermediate full/empty (4), empty (5), UV-irradiated intermediate full/empty (6), and UV-irradiated empty (7) particles, lane 8: virus particles from the IOD-PBS gradient, lanes 9-11: VIS-Ringer gradient fractions corresponding to full (9), intermediate full/empty (10), and empty (11) particles, M: size markers.

Panels c, d: Electron micrographs showing empty-particle fractions before (c) and after (d) UV-irradiation.

Figure 9:
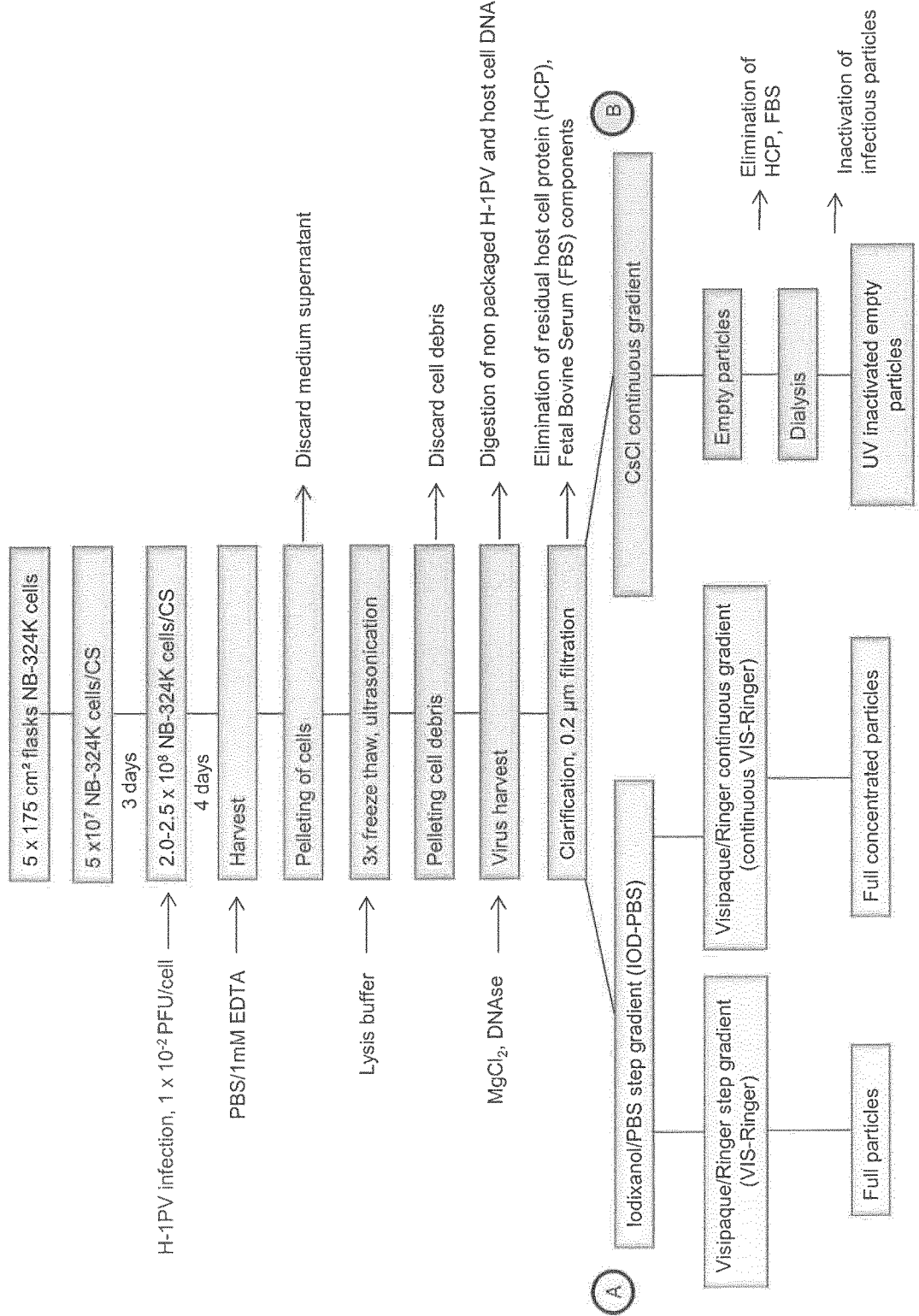

FIG. 9: Flow diagram of H-1PV production with the recommended procedures for preparing infectious (A) and empty (B) particles Thus, the present invention relates to a method for producing full active parvovirus particles and empty inactive parvovirus particles, said method comprising:

(a) providing the producer cell line NB-324K;

(b) growing the cell line under suitable conditions and infecting the cells at a cell density from 2.0 to $5.0 \times 10^4$ cells/cm$^2$ with the parvovirus at a MOI of 0.5 to $2 \times 10^{-2}$ PFU/cells;

(c) harvesting the cells 2 to 6 days post-infection and obtaining a cell pellet by centrifugation;

(d) subjecting the resuspended cell pellet to a mechanical, physical or chemical cell lysis method for obtaining a parvovirus containing cell lysate;

(e) sonicating the cell lysate and subjecting it to DNAse treatment;

(f) clarifying the DNAse-treated parvovirus harvest by filtration; and (g1) purifying the parvovirus by two successive density gradient ultracentrifugations, wherein the first gradient is a Iodixanol/PBS step gradient and the second gradient is a Iodixanol/Ringer step gradient or a Iodixanol/Ringer continuous gradient for obtaining full active parvovirus particles in one fraction and empty parvovirus particles in another fraction; or (g2) purifying the parvovirus by a continuous CsCl gradient ultracentrifugation for obtaining empty parvovirus particles.

For optimum results, the producer cell line NB-324K is characterized by (a) a viability of at least 95%, (b) a passage number below 20 (c) lack of mycoplasma contamination, and (d) lack of SV 40 production.

Preferably, the method of the present invention is used for production/purification of the parvovirus H1-PV.

The person skilled in the art knows common conditions for growing the producer cell line and for infecting the cells with the parvovirus. Usually, the cells are cultured at 37° C., e.g., in minimal essential medium with heat-inactivated fetal bovine serum (e.g. FBS 5%) in a 5% $CO_2$ atmosphere. Preferably, the medium should be supplemented with penicillin, streptomycin and L-glutamine.

In a preferred embodiment of the present invention, the cell density of step (b) is from 3.0 to $4.0 \times 10^4$ cells/cm$^2$.

In a further preferred embodiment of the method of the present invention, virus production is performed in a single use cell culture system, preferably a 10-layer cell culture chamber, e.g. CellSTACK® (CS) chamber. Further upscaling may be achieved with a 40-layer CS chamber or a carrier system.

Preferably, for harvesting, the culture medium is aspirated and infected cells are treated with a suitable buffer and/or enzyme e.g. PBS-EDTA or Trypsin. The medium supernatant and detached cells are centrifuged for obtaining a cell pellet, preferably at 5,000×g, preferably for about 5 min. The person skilled in the art knows suitable mechanical, chemical or physical methods for releasing the parvovirus from the producer cells. Preferably, this can be done by freeze/thaw cycles, ultrasound treatment and/or Triton® S100 treatment. The person skilled in the art also knows suitable methods for sonicating the cells and subsequent DNAse treatment. E.g., the cells can be sonicated at 30 to 70 W for a sufficient time and DNAse-treatment is carried out with 20-80 U/ml DNAse, usually at 37° C. for 10 to 50 min.

For the further purification and for the enrichment of full active parvoviral particles Iodixanol/PBS (IOD-PBS) and VISIPAQUE®/Ringer (Vis-Ringer) density gradients are carried out. These steps are described in further detail below.

The above mentioned "Iodixanol" is a synonym for "VISIPAQUE®" (for human injection use) or "Iodixanolum" (research grade). The chemical structure is

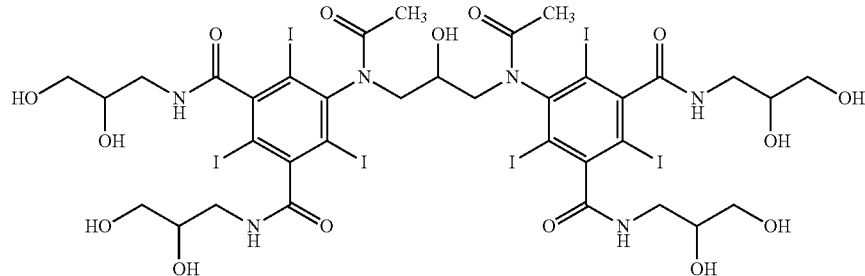 [SMILES: CC(=O)N(CC(O)CN(C(C)=O)c1c(I)c(C(=O)NCC(O)CO)c(I)c(C(=O)NCC(O)CO)c1I)c1c(I)c(C(=O)NCC(O)CO)c(I)c(C(=O)NCC(O)CO)c1I]

The IUPAC name is 5-[acetyl-[3-[N-acetyl-3,5-bis(2,3-dihydroxypropylcarbamoyl)2,4,6,-triiod-oanilino]2-hydroxypropyl]amino]-1-N,3,N-bis(2,3-dihydroxypropyl)-2,4,6-tri-iodobenzene-1,3-dicarboxamide. The CAS number is 92339-11-2. VISIPAQUE® is also a well known contrast agent for CT imaging.

(i) IOD-PBS and Vis-Ringer Density Gradients

Thus, to eliminate proteins, a step density gradient centrifugation was done as described by Zolotukhin (Zolotukhin et al., 1999). In a preferred embodiment, Quickseal tubes (Beckman, Germany, e.g. 25.times.89 mm) were filled with 10-50 ml, preferably 20 ml, virus suspension. This suspension was underlaid with two to five, e.g. four, layers of Iodixanol (Alexis Shield, Norway) in buffer, e.g. PBS. Preferred Iodixanol concentrations: 15, 25, 40, and 60%. Ultracentrifugation was performed for a suitable time and velocity in an ultracentrifuge, preferably 2 h at 4° C. in a 50.2 Ti rotor at 50,000 rpm (Beckman, L870M, Germany) that corresponds to 227,220 relative centrifugal force (RCF). Usually, 3.5 ml virus suspension was collected from the 40% Iodixanol layer. Afterwards, a second density gradient centrifugation was performed with VISIPAQUE® (GE Healthcare, Norway) diluted in buffer, preferably Ringer solution (B. Braun, Germany) for further protein elimination and separation of full from empty particles. In a preferred embodiment, Quickseal tubes (e.g. 25×89 mm) were filled with virus suspension from the IOD-PBS density gradient, diluted at least 1:2.5 in buffer, e.g. Ringer solution. Then 1-10 ml (e.g. 5 ml) of 25%, 1-10 ml (e.g. 4 ml) of 40%, and 1-10 ml (e.g. 4 ml) of 55% VISIPAQUE® in Ringer solution were underlaid. For detection of the 40% layer, a reference gradient was made, where the 25% and 55% VISIPAQUE®/Ringer phases were colored with phenol red. Additionally, the 40% phase was labeled outside on the sample tube. Ultracentrifugation was performed under suitable conditions, e.g. for 2 h at 4° C. in a 50.2 Ti rotor at 50,000 rpm. Two fractions of the 40% phase were then collected with a syringe and hollow needle: preferably 1-5 ml, e.g. 2.5 ml, of the full-particle fraction (lower band in the 40% layer) and preferably 0.1-1.5 ml, e.g. 800 µl, of the empty-particle fraction (upper band in the 40% layer). The refraction index of a 5 µl sample was measured with a refractometer (AR200, Reichert Analytical Instruments, Germany) and the densities of the regions from which the fractions were taken were calculated with a reference table for Iodixanol (AXIS-SHIELD, Norway).

(ii) Continuous Vis-Ringer Gradient

For the continuous Vis-Ringer gradient, Quickseal tubes were filled with virus suspension diluted in Ringer solution to a refraction index of about 1.3 to 1.4, e.g. 1.3815, (corresponding to 30% VISIPAQUE®). The virus suspension was underlaid with 0.1-1 ml, preferably 0.5 ml, of 60-70%, preferably 65.2%, VISIPAQUE® cushion, and the tube was completely filled with preferably 30% VISIPAQUE®/Ringer solution. Ultracentrifugation was performed under suitable conditions, preferably for 10 h at 4° C. in a 70.1 Ti rotor at 63,000 rpm. Fractions of about 500 µl were collected from the bottom under controlled dripping.

As mentioned above, according to the present invention, to obtain empty inactive particles a CsCl density gradient is carried out. A CsCl density gradient was established as described previously (Paradiso, 1981). In a preferred embodiment, polyallomere centrifuge tubes (Beckmann, Germany; 14×95 mm) were filled with 1-10 ml, preferably 5 ml, CsCl at about 1.4 g/cm$^3$ density and overlaid with 0.1-2 ml, preferably 1 ml, 1 M saccharose followed by 5 ml virus suspension. Ultracentrifugation was performed at suitable conditions, preferably 15° C. for at least 20 h at 39,000 rpm in an SW41 rotor. Different fractions were collected from the bottom (e.g. fr# 1: 500 µl, fr# 2: 300 µl, fr# 3-20: 200 µl) and the capsid (physical particle, PP) content was measured by means of the new ELISA ($C_{aps}$id-ELISA) described below or by hemagglutination assay. For detection of hemagglutination units (Kongsvik and Toolan, 1972), the fractions were diluted 1:10 to 1:50, e.g. 1:25, in buffer (e.g. PBS) and further diluted serially (e.g. 1:2) in a round-bottom 96-well plate (Greiner Bio-One, Germany). Next, a suitable amount, preferably 25 µl, of a 2% suspension of guinea pig red cells (Charles River Laboratories, Germany) in PBS was added. The plate was incubated, e.g. for 1 h at 4° C., and the titer read as the highest dilution at which hemagglutination was complete. The refraction index was measured and the density calculated according to a reference table for CsCl (Griffith, 2006). Fractions containing full or empty capsids were pooled and directly dialyzed, e.g. against 1,000 volumes of VTE buffer for approximately 30 min at room temperature. This was followed by several, preferably three, dialysis cycles at 4° C. to eliminate the toxic CsCl.

In another preferred embodiment empty particles may also be obtained after the Vis-Ringer gradient centrifugation. As mentioned above the empty-particle fraction is located as the upper band in the 40% layer.

For inactivation of residual infectious particles in the empty-particle pool, the empty-particle fraction is subjected to a deactivation step. Suitable deactivation methods are UV inactivation (Tuynder et al, 2004), chemical, physical and/or thermical methods. The UV inactivation is particularly preferred.

The present invention also provides a method for determining the ratio of native parvovirus capsids to non-assembled capsid proteins or denatured capsids. In a preferred embodiment, the ratio is determined by using a monoclonal antibody. A particularly preferred monoclonal antibody is the monoclonal antibody BL-H1 (DSM ACC 3030). The person skilled in the art knows suitable formats for use of this antibody, e.g., ELISA.

The following examples are intended to illustrate, but not to limit the invention. While such examples are typical of those that might be used, other methods known to those skilled in the art may alternatively be utilized.

EXAMPLE 1

Material and Methods (A) Producer Cell Line, H-1PV Virus Stock

NB-324K human newborn kidney cells transformed with simian virus 40 (SV40) (Tattersall and Bratton, 1983) were cultured at 37° C. in minimum essential medium (MEM, Sigma, Germany) with 5% heat-inactivated fetal bovine serum (FBS, Biowest, France) in a 5% $CO_2$ atmosphere. The medium was supplemented with 100 U/ml penicillin, 100 µg/ml streptomycin, and 2 mM L-glutamine (Life Technologies, Germany). For production, NB-324K cells propagated in 175-$cm^2$ Y-flasks (Nunc, Denmark) were seeded into a 10-layer CeliSTACK® culture chamber (Corning, Germany) with a 6,360 $cm^2$ growth area. Cell density and viability were measured by staining living cells with 0.4% trypan blue (Invitrogen™, Germany). Cells were counted with a Countess® Cell counter (Life Technologies, Germany). An in-house purified H-1PV virus stock was used to infect the cells.

(B) H-1PV Production

A 10-layer CellSTACK® (CS) was chosen as a convenient single-use production system. For simultaneous cell seeding and infection, NB-324K cells were seeded at $3.6 \times 10^4$ cells/$cm^2$ into the 10-layer CS and infected immediately with H-1PV at a multiplicity of infection (MOI) of 0.01 plaque forming units (PFU) per cell. The pH during infection was 7.0±0.1. The infected cells were incubated for 4 days at 37° C. under 5% $CO_2$ until the cytopathic effect (CPE), measured as the percentage of dead and detached cells observed under a microscope, reached at least 30%. For non-simultaneous seeding and infection, NB-324K cells were seeded at $7.9 \times 10^3$ cells/$cm^2$ into a 10-layer CS and allowed to grow for three days, by which time they had reached a density of approximately $3.6 \times 10^4$ cells/$cm^2$, as measured on a control-flask culture. These anchored cells were then infected at a MOI of 0.01 PFU/cell and incubated for 4 days as described above. For harvesting, the medium was aspirated and infected cells were treated with PBS/1 mM EDTA. The medium supernatant and detached cells were centrifuged for 5 min at 5,000×g. The pellet was washed with PBS, resuspended in Virus Tris/EDTA buffer, pH 8.7 (VTE) containing 0.05 M Tris HCl, 0.5 mM EDTA, and subjected to three freeze/thaw cycles. After centrifugation for 5 min at 5,000×g, cell debris were discarded. The cell lysate was then sonicated at 48 W for 1 min in a Sonorex Super 10 P ultrasonic homogenizer (Bandelin, Germany) and treated with DNAse (50 U/ml, Sigma, Germany) for 30 min at 37° C.

(C) H-1PV Purification

The DNase-treated virus harvest was clarified by filtration through a 0.2-µm Sartolab® P20 Plus filter (Sartorius, Germany). Two different methods were used to purify the virus, either two consecutive step gradients—one with Iodixanol-PBS (IOD-PBS) and one with VISIPAQUE®-Ringer (VIS-Ringer)—or a cesium chloride density gradient followed by dialysis against VTE buffer.

To eliminate proteins, a step density gradient centrifugation was done as described by Zolotukhin (Zolotukhin et al., 1999). For this, 25×89 mm Quickseal tubes (Beckmann, Germany) were filled with 20 ml virus suspension. This suspension was underlaid with four layers of Iodixanol (Alexis Shield, Norway) in PBS (Iodixanol concentrations: 15, 25, 40, and 60%). Ultracentrifugation was performed for 2 h at 4° C. in a 50.2 Ti rotor at 50,000 rpm (Beckmann, L870M, Germany) that corresponds to 227,220 relative centrifugal force (RCF). Usually, 3.5 ml virus suspension was collected from the 40% Iodixanol layer. Afterwards, a second density gradient centrifugation was performed with VISIPAQUE® (GE Healthcare, Norway) diluted in Ringer solution (B. Braun, Germany) for further protein elimination and separation of full from empty particles. For this, 25×89 mm Quickseal tubes were filled with virus suspension from the IOD-PBS density gradient, diluted at least 1:2.5 in Ringer solution. Then 5 ml of 25%, 4 ml of 40%, and 4 ml of 55% VISIPAQUE® in Ringer solution were underlaid. For detection of the 40% layer, a reference gradient was made, where the 25% and 55% VISIPAQUE®/Ringer phases were colored with phenol red. Additionally, the 40% phase was labeled outside on the sample tube. Ultracentrifugation was performed for 2 h at 4° C. in a 50.2 Ti rotor at 50,000 rpm. Two fractions of the 40% phase were then collected with a syringe and hollow needle: 2.5 ml of the full-particle fraction (lower band in the 40% layer) and 800 µl of the empty-particle fraction (upper band in the 40% layer). The refraction index of a 5 µl sample was measured with a refractometer (AR200, Reichert Analytical Instruments, Germany) and the densities of the regions from which the fractions were taken were calculated with a reference table for Iodixanol (AXIS-SHIELD, Norway).

(ii) Continuous Vis-Ringer Gradient

For the continuous Vis-Ringer gradient, Quickseal tubes were filled with virus suspension diluted in Ringer solution to a refraction index of 1.3815 (corresponding to 30% VISIPAQUE®). The virus suspension was underlaid with 0.5 ml of 65.2% VISIPAQUE® cushion, and the tube was completely filled with 30% VISIPAQUE®/Ringer solution. Ultracentrifugation was performed for 10 h at 4° C. in a 70.1 Ti rotor at 63,000 rpm. Fractions of about 500 µl were collected from the bottom under controlled dripping.

(iii) Cesium Chloride Density Gradient and Hemagglutination Assay

A CsCl density gradient was established as described previously (Paradiso, 1981). For this, 14×95 mm polyallomere centrifuge tubes (Beckmann, Germany) were filled with 5 ml CsCl at 1.4 g/$cm^3$ density and overlaid with 1 ml 1 M saccharose followed by 5 ml virus suspension. Ultracentrifugation was performed at 15° C. for at least 20 h at 39,000 rpm in an SW41 rotor. Different fractions were collected from the bottom (fr# 1: 500 µl, fr# 2: 300 µl, fr# 3-20: 200 µl) and the capsid (physical particle, PP) content was measured by means of the new ELISA (Capsid-ELISA) described in this paper or by hemagglutination assay. For detection of hemagglutination units (Kongsvik and Toolan, 1972), the fractions were diluted 1:25 in PBS and further diluted serially 1:2 in a round-bottom 96-well plate (Greiner Bio-One, Germany). Next, 25 µl of a 2% suspension of guinea pig red cells (Charles River Laboratories, Germany) in PBS was added. The plate was incubated for 1 h at 4° C. and the titer read as the highest dilution at which hemagglutination was complete. The refraction index was measured and the density calculated according to a reference table for CsCl (Griffith, 2006). Fractions containing full or empty capsids were pooled and directly dialyzed against 1,000 volumes of VTE buffer for approximately 30 min at room temperature. This was followed by three dialysis cycles at 4° C. to eliminate the toxic CsCl.

(D) UV Inactivation of the Empty-Particle Pool

For inactivation of residual infectious particles in the empty-particle pool, 500 µl of empty-particle fraction was placed at the center of a 6-cm dish (Greiner Bio-One, Germany) under a sterile laminar flow hood. A UV lamp (Type NU-4, Herolab, Germany) emitting at 254 nm was used to irradiate the sample at 0.5 mW/cm$^2$, as measured with a radiometer (VLX-3W, Benda, Germany). The sample was irradiated 4 times for 2 min with intervals of 5 min without UV.

(E) Virus Quantification and Characterization (i) Plaque Formation Assay

Plaque assays were done essentially as described by Tattersall and Bratton, 1983. NB-324K cells were grown in monolayer cultures in MEM medium containing 5% FBS, 100 µg/ml penicillin, 100 µg/ml streptomycin, and 2 mM L-glutamine. They were infected at 60% confluence with serial dilutions of H-1PV and incubated for 1 h at 37° C. Then the inoculum was replaced with a bacto-agar overlay (1.7% in MEM containing 5% FBS). On day four post-infection, living cells were stained for 18-24 h by addition of 0.02% toluylene red staining solution (Sigma, Germany) containing bacto-agar (Becton Dickinson, Germany). The dishes were incubated at 37° C. under 5% $CO_2$. Plaque-forming units were counted 5 days post-infection on a light box and their concentration expressed in PFU/ml.

(ii) DNA Hybridization Assay for Infectious H-1PV

NB-324K cells (7.6×10$^3$ cells/well) were seeded into a 96-well plate 24 h prior to infection with H-1PV. They were infected with 10-fold serial dilutions of H-1PV and incubated for 72 h at 37° C. under 5% $CO_2$. After freezing at −80° C. and alkaline lysis (1.5 M NaOH), their DNA was transferred to a nylon membrane, cross-linked with a CL-1000 Ultraviolet Crosslinker (UVP, USA) and hybridized with an NS1-specific $^{32}$P-radiolabeled probe prior to autoradiography. Virus titration was performed in duplicate and the titer expressed in infectious units (IU) per ml (Lacroix et al., 2010).

(iii) Determination of Genome-Containing Viral Particles

The number of genome-containing viral particles (GP) was determined by Q-PCR, essentially as described previously (Lacroix et al., 2010). Each well received 20 µl reaction mix containing 1× Premix Ex Taq™ (TaKaRa, France), 0.3 µM labeled NS1-TaqManm probe, each primer at 0.3 µM, and 3 µl template. Q-PCR was run in an Abi Prism 7900 HT Sequence Detection System and results were processed with the SDS 2.1 software (Applied Biosystems, Germany).

(iv) H-1PV Capsid-ELISA

An ELISA was developed for detection of capsids (full or empty, henceforth called "physical particles" or PP). A flexible 96-well, U-bottomed plate (BD Falcon, N.J.) was coated overnight at 4° C. with 100 µl monoclonal antibody BL-H1 at 2 ng/µl in PBS. The development of this antibody (Leuchs et al., 2010) is described below. The coating solution was removed, 200 µl blocking buffer (2 mg/ml casein (Sigma, Germany) and 0.05% Tween 20 (Sigma, Germany) in PBS) was added to each well, and the mixture incubated for 1 h at 37° C. Blocking buffer was aspirated and the wells were washed with PBS, 0.05% Tween 20, after which the positive control, the negative control, the sample, and serial dilutions of H-1PV standard (all of them in PBS buffer) were plated in duplicate at 100 µl/well. The plate was incubated for 1 h at 37° C. The reaction mixture was aspirated and the wells were washed. Next, 100 µl mAb BL-H1 labeled with horseradish peroxidase (0.1 µg/ml) was added to each well and incubated for 1 h at 37° C. Samples were aspirated and the wells were washed with PBS, 0.05% Tween 20. After addition of 100 µl 3,3',5,5'-tetramethylbenzidine (Sigma, Germany) to each well, the plate was incubated for 15 min at room temperature in the dark. The reaction was stopped by adding 100 µl of 1 M $H_2SO_4$ per well. Sample absorbance was measured at 450 nm with an Ascent Multiscan Plate Reader (Thermo Fisher Scientific, Germany).

(v) Bicinchoninic Acid (BCA) and Bradford Assays

Protein concentration was determined with the Pierce® BCA Protein Assay Kit 23227 (Pierce, USA) in the 5-250 µg/ml working range. The protein concentration was determined with a bovine serum albumin (BSA) standard and measured with Nanodrop 2000. The Bradford Assay was performed in a 96-well plate in the 50-2000 µg/ml working range, with BSA as standard (Sigma, Germany).

(vi) SDS-PAGE, Silver Staining, and Western Blotting

To assess the purity of virus preparations, a 10% SDS-PAGE was performed (SERVA Electrophoresis, Germany), followed by silver staining (Invitrogen, CA) and western blotting. For viral capsid protein (VP) detection, polyclonal rabbit anti-VP (αVP) (provided by C. Dinsart, DKFZ, Heidelberg) and a horseradish-peroxidase-conjugated anti-rabbit IgG (Amersham™ ECL Western Blotting Analysis) were used.

(vii) DNA Measurement

DNA was quantified by measuring the absorbance at 260 nm with a Nanodrop spectrophotometer. Human genomic DNA in the virus preparations was quantified by Q-PCR with the Quantifiler® Human DNA Quantification Kit (Applied Biosystems, Germany) for detection of h-TERT (human telomerase reverse transcriptase), according to the manufacturer's instructions. The detection limit was 26 ng/ml and the amplicon size was 62 bp. As positive control, NB-324K cell genomic DNA was used.

(viii) Endotoxins and Sterility

Contamination by endotoxins was tested with the Endosafe® Gel-Clot Limulus Amebocyte Lysate Assay (Charles River Laboratories, Germany). The sensitivity of the assay was 0.25 endotoxin unit (EU) per milliliter. Each H-1PV preparation was checked for the absence of bacterial or fungal contamination by incubating 2.5 µl of the preparation on soy/peptone-agar for 5 days at 37° C.

(ix) Electron Microscopy

For qualitative analysis of virus preparations, electron microscopy pictures were taken. For this, 5 µl virus suspension was added to a ready-to-use carbon-coated copper grid and incubated for 2 min. The grid was then washed with 5 µl bidest water and coated with 2% uranyl acetate for 30 s. The drops were absorbed from the grid with Whatman 50 filter paper and the grid was dried for approximately 1 min. Photos were taken with a Zeiss transmission electron microscope at 20,100× magnification.

(F) Development and Characterization of the Monoclonal Antibody BL-H-1

To generate a monoclonal antibody against H-1PV capsids (PP), Balb/c mice (Charles River, Germany) were immunized intraperitoneally, 3 times over a 3-month period, with $1.2 \times 10^8$ PFU each time. One week after the last H-1PV injection, their spleens were removed and spleen cells were fused with X63/Ag8 lymphoma cells (Kuck et al., 2007; Wobus et al., 2000). The hybridoma cells were propagated and the supernatants from single-clone were screened by western dot blotting against H-1PV. Positive wells were selected by single-colony analysis, and after three selection rounds, the selected hybridoma cells were used to produce BL-H1 antibodies in a CELLine 1000 bioreactor (Integra Biosciences AG, Switzerland). RPMI 1640 medium supplemented with 10% FBS, 100 µg/ml penicillin, 100 µg/ml streptomycin, 2 mM L-glutamine, 20 mM Hepes pH 7.2 was used to culture the hybridoma cells. The subclass of the BL-H1 antibody was determined with the Amersham mouse monoclonal antibody isotyping kit (Braunschweig, Germany). Purification was done with the HiTrap™ Protein A HP affinity column kit (GE Healthcare, Sweden) and the Akta prime system (GE Healthcare, Germany). The $IgG_{2a}$ concentration was determined with the Mouse $IgG_{2a}$ ELISA Set (BD Biosciences, Germany).

(i) H-1PV Analysis by Western Dot Blotting

Purified H-1PV ($1 \times 10^8$ PFU/dot) or sucrose density gradient fractions (diluted 1:10 in 100 µl PBS) were transferred to a nitrocellulose membrane (AppliChem, Germany) with a vacuum blotter. Washing steps were carried out with PBS, 0.05% Tween 20. The membrane was blocked for 1 h with PBS containing 5% skimmed milk powder. For hybridoma screening, 40 µl undiluted hybridoma supernatant was incubated for at least 3 h. For sucrose gradient analysis, either purified mAb BL-H1 (1:1,000) or αVP antibody (1:500 diluted) was used. The membrane was then washed for 30 min at RT and incubated with secondary peroxidase-coupled goat anti-mouse (GE Healthcare, Germany) or goat anti-rabbit antibody (GE Healthcare, Germany) in PBS. Detection was done with ECL Plus and Hyperfilm ECL (Amersham Biosciences GmbH, Germany).

(ii) Sucrose Density Gradient Fractionation of Assembled and Non-Assembled Viral Capsid Proteins Extract was prepared from 293T cells (CRL-11268, American Tissue Culture Collection) transfected with an infectious H-1PV molecular clone (Kestler et al., 1999) and harvested 72 h post-transfection. One ml of extract was transferred to a 10-50% linear sucrose gradient. Centrifugation was performed at 4° C. for 3.3 h at 28,000 rpm in a TST 41.14 (Kontron) rotor. Fractions (400 µl) were collected and analyzed by western blotting and hemagglutination assay. The fractions were also assayed for infectivity and genome-containing particles.

EXAMPLE 2

Characterization of H1-PV

One of the aims of the present invention was to standardize the H-1PV manufacturing procedure. This involved characterizing each upstream and downstream process step, ensuring reproducibility, and fully characterizing the identity, purity, and safety of the final product in order to establish standard operating procedures.

Two alternative methods of cell preparation and infection were tested upstream from the core production process. Two different purification tracks downstream from core production were also compared. Table 1 summarizes the assays used to characterize intermediate steps in the production procedure and the final product as described below. To quantify physical particles more conveniently, it was necessary to establish a new assay, described below.

TABLE 1

Assays used for the quantitative and qualitative characterization of H-1PV stocks

| Assay | Type of characterization | Unit |
|---|---|---|
| Plaque formation assay | Biological assay for virus multiplication and spread. Virus titers expressed in plaque forming units | PFU/ml |
| DNA hybridization assay for infectivity | In situ assay for virus infection and DNA replication. Virus titers expressed in infectious units | IU/ml |
| Viral genome quantification by real-time PCR (Q-PCR) | Physical characterization for presence of genome containing viral particles | GP/ml |
| Capsid-ELISA | Physical determination of assembled viral particles, expressed in physical particles | PP/ml |
| Hemagglutination assay | Physical characterization for virus mediated guinea pig erythrocytes agglutination. Virus titer expressed in hemagglutination units | HAU/ml |
| Refraction index measurement | Physical determination of density from the refractive index (RI) | mg/cm$^3$ |
| Bicinchoninic and Bradford assays | Colorimetric protein quantification | µg protein/ml |
| SDS-PAGE and Western blot | Determination of purity and identity of viral proteins | — |
| Q-PCR with h-TERT Quantifiler | Quantification of cell genomic DNA | ng DNA/ml |
| $A_{260}$ measurement | Spectrometric determination of DNA | ng DNA/ml |
| Electron microscopy | Ultrastructural visualization of virus stocks | — |
| LAL assay | Determination of endotoxin units | EU/ml |
| Sterility assay | Determination of bacteria and fungi colony-forming units on soy/peptone-agar plates | CFU/ml |

Figure 1:
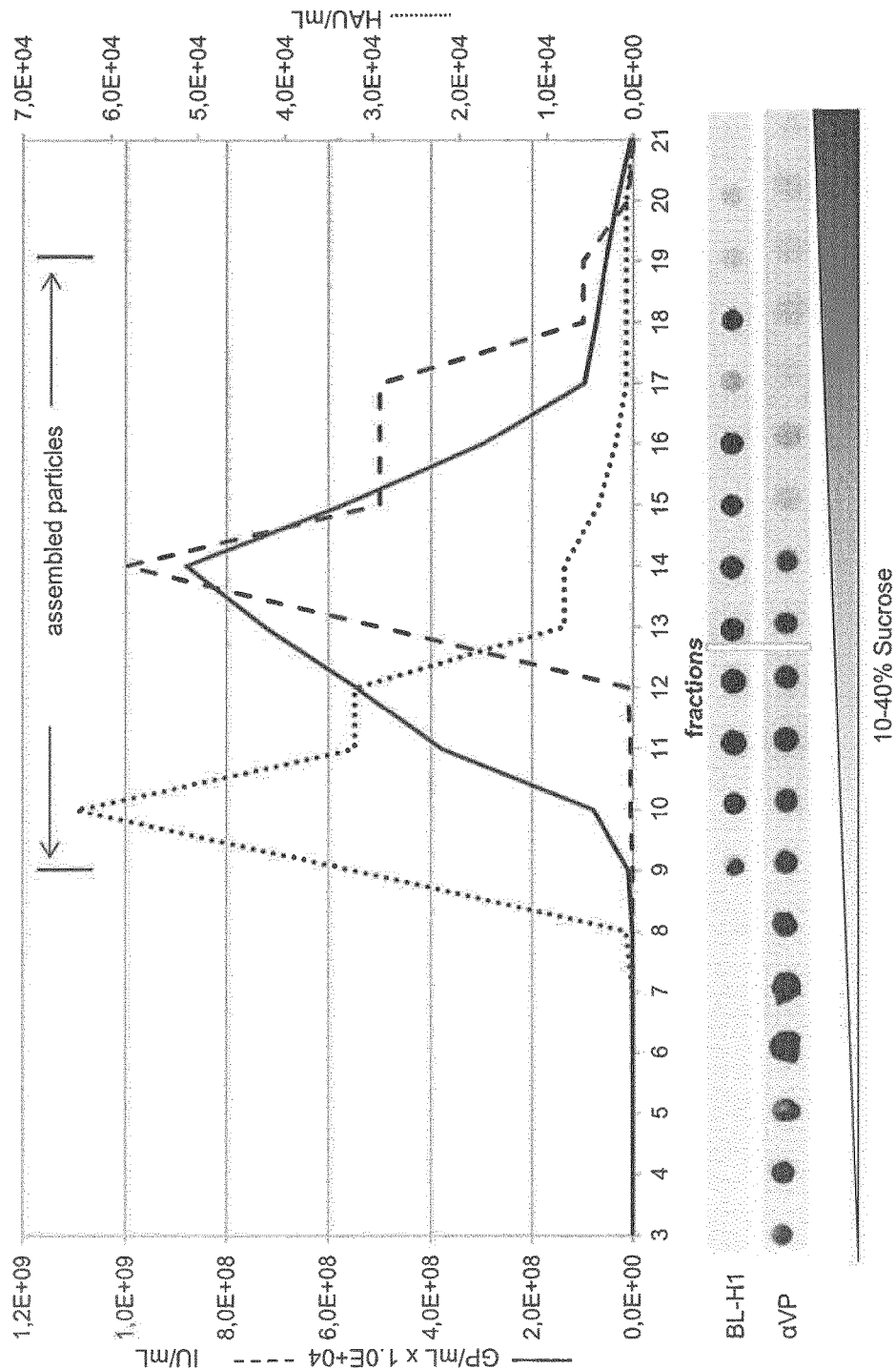
FIG. 1: Characterization of antibodies targeting viral capsid proteins

Two goals of this study were to separate full from empty particles and to determine the particle-to-infectivity ratio of the final product. Determining this ratio, which should influence both the therapeutic efficacy of parvoviral treatment and the expected immune response, requires determining the total number of physical particles (Rajendran et al.). To develop a convenient method for quantifying PP, we generated a monoclonal antibody against H-1PV, which recognizes native capsids but fails to recognize non-assembled capsid proteins or denatured capsids. This antibody, called BL-H1, is of type $IgG_{2a}$. Its specificity is illustrated in FIG. 1, which shows the results of various analyses performed on the fractions obtained after sucrose density centrifugation of extracts of 293T cells transfected with an infectious H-1PV molecular clone. On western dot blots, the only fractions giving a signal with both αVP antiserum (predominantly recognizing non-assembled capsid proteins) and mAb BL-H1 were fractions 9 to 18. These fractions were found to contain assembled capsids, as demonstrated by measuring hemagglutination, GPs and IU. BL-H1 did not react with fractions 3 to 8, containing non-assembled or partially assembled capsid proteins. Fractions 9 to 19 included both empty and genome-containing particles, with infectious particles concentrating in fractions 12 to 19. Interestingly, although the hemagglutination and BL-H1 signals were confined to the same region of the gradients, the latter peak was shifted towards higher densities. Furthermore, BL-H1 was found not to react with denatured capsid proteins and showed no cross-reaction with capsids of the closely related *protoparvovirus* minute virus of mice (data not shown).

EXAMPLE 3

ELISA for H-1PV Capsid Quantification

To quantify physical particles throughout H-1PV production, we developed a "Capsid-ELISA" using mAb BL-H1. To standardize the ELISA, H-1PV was mixed with appropriate dilutions of a stock of adenovirus type 5 (Ad5, American Type Culture Collection) of known titer and the mixtures were visualized by electron microscopy. On 8 randomly chosen pictures, H-1PV and Ad5 particles were counted and the number of H-1PV particles was determined in relation to the known Ad5 titer. The ELISA showed a reproducible linear relationship between the number of PP (in the range $2.5 \times 10^9$ to $3.9 \times 10^7$ PP) and absorbance at 450 nm (FIG. 2). Two of the tested dilutions, QC-L (low virion load) and QC-M (medium virion load) were used as quality controls in subsequent assays. When CsCl density gradient centrifugation was used to separate empty from full H-1PV capsids, this ELISA allowed quantification of both. This is illustrated in FIG. 3, showing the distribution of capsids (as determined by our Capsid-ELISA and by hemagglutination assay) and that of genome-containing particles after centrifugation. The two methods for detecting physical particles gave superimposable profiles, with a major peak for empty capsids and two minor ones for full capsids. PCR detection of DNA-containing capsids likewise revealed two density groups (fractions 4-6 and fractions 7-10). While the intermediate density particles may consist of defective interfering particles (Faust and Ward, 1979), their nature was not analyzed further. Nevertheless, our results clearly show that the developed ELISA is suitable for routine detection of physical particles.

EXAMPLE 4

Large-Scale Production of H-1PV (A) Optimization of Cell Seeding and Infection

We first optimized the cell density at the time of infection, the MOI, and the time of harvest. The highest virus yields were obtained with a cell density of $3.6 \times 10^4$ cells/cm$^2$, a MOI of $1 \times 10^{-2}$ PFU/cell, and harvesting 4 days post-infection, with approximately 30% CPE (data not shown). These conditions were used subsequently in all production experiments, the only difference being that some cells were grown in 175-cm$^2$ Y-flasks, harvested, transferred to a CS, and infected immediately, while others were allowed to grow in the CS for three days prior to infection.

Table 2a shows that cells infected and seeded simultaneously and cells allowed to grow for three days in the CS prior to infection did not differ significantly as regards either virus production per infected cell or virus release into the supernatant per infected cell. In both cases, approximately $1 \times 10^3$ PFU were produced per infected cell, corresponding to an average yield of $2 \times 10^{11}$ PFU per 10-layer CellSTACK®. Protein concentrations in the virus harvests obtained were also similar for the two procedures ($2 \times 10^3$ µg/ml), indicating that the two cultures reached the same density at harvest time. As infection three days post-seeding saved working time and material as compared to simultaneous seeding and infection, the former approach was adopted. The culture medium supernatant contained only 10% of the total PFUs, at relatively low concentration (around $10^7$ PFU/ml). As concentrating the supernatant was cumbersome, time consuming, and inefficient, this fraction was discarded in routine productions.

TABLE 2a

Infectious-particle recoveries after two different seeding/infection procedures

| | Seeding/infection procedure | PFU/infected cell | µg/ml protein |
|---|---|---|---|
| Cell extract | 3 days in CS prior to infection | 1.1 ± 1.8E+03 | 2.0 ± 0.9E+03 |
| | simultaneous seeding and infection | 0.8 ± 0.4E+03 | 1.7 ± 0.4E+03 |
| Medium supernatant | 3 days in CS prior to infection | 0.1 ± 0.2E+03 | 0.8 ± 0.4E+03 |
| | simultaneous seeding and infection | 0.5 ± 0.4E+03 | 0.9 ± 0.4E+03 |

Means with standard deviations of infectious particle and protein concentrations in virus harvests. Concentrations in cell extracts (20 ml/CS) and medium supernatants (1000 ml/CS) were calculated from 5 or more independent productions.

(B) Reproducibility of the Standardized Upstream Process and H-1PV Yields

As shown in FIG. 4, the H-1PV virion yield was highly reproducible over five independent productions. The particle-to-infectivity ratio (PP/PFU) and the proportion of genome-containing particles (PP/GP) were also similar between these productions. The ratio of PFU to GP to PP was $1:7 \times 10^2:5 \times 10^3$. It thus appeared that on average an indicator cell had to be infected with $7 \times 10^2$ genome-containing virions to undergo a productive infection. About 14% of the total virions contained an encapsidated genome.

EXAMPLE 5

Purification of H-1PV (A) DNase Digestion and Clarification of H-1PV Harvests

Unprocessed virus harvests were treated with DNase to digest non-encapsidated viral and host-cell DNA and then clarified by filtration through a Sartolab® P20 Plus filter. Results obtained for five individual batches showed the significance of these steps. As measured with the human DNA Quantification Kit, 99.8% of the host-cell DNA was removed by DNase treatment. Yet only 37% of the total DNA was eliminated, as determined by $A_{260\ nm}$ measurement. The residual DNA might be protected viral genomes and/or cellular DNA fragments smaller than the h-TERT amplicons (62 bp) used for DNA detection. As illustrated in FIG. 8a, the filtration step eliminated 24% of the host-cell and FBS-derived proteins. More than 80% of the infectious virions and 100% of the physical particles were recovered after clarification (Table 2b). In conclusion, this first purification step is fast and eliminates significant amounts of foreign DNA and proteins.

TABLE 2b

Virus harvest yields (cell extracts) and recoveries after clarification

|  | Virus harvest | After clarification | Recovery % |
|---|---|---|---|
| PFU/ml | 7.2 ± 6.4E+09 | 5.8 ± 6.1E+09 | 81 |
| GP/ml | 4.8 ± 2.7E+12 | 6.1 ± 3.4E+12 | 127 |
| PP/ml | 1.7 ± 0.8E+13 | 1.9 ± 1.3E+13 | 111 |
| protein µg/ml | 2.1 ± 0.9E+03 | 1.6 ± 0.4E+03 | 76 |

Virus recovered from one 10-layer CS was dissolved in 20 ml VTE and the PFU, GP and PP were determined. Protein concentration was quantified by colorimetric assay. Means with standard deviations for 5 independent productions are shown. Recovery was calculated after clarification of the virus harvest by 0.2 µm filtration.

(B) Separation of Full from Empty Particles

Figure 5A:
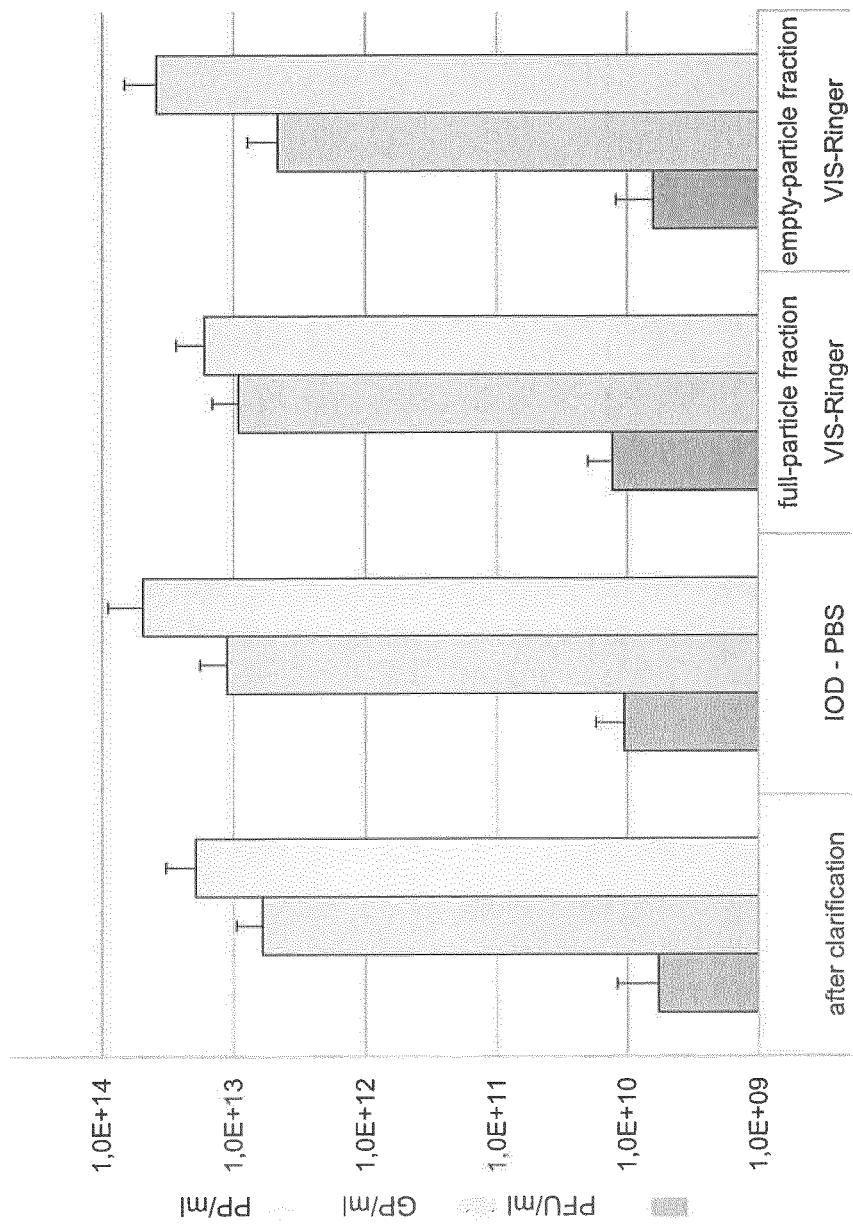

To separate full from empty H-1PV particles, two gradient centrifugation procedures were compared. Similar results were obtained with five individual H-1PV harvests from two 10-layer CS cultures. After clarification, each harvest was split into two equal parts, one of which was purified by two consecutive step gradients: IOD-PBS and VIS-Ringer, the Ringer and VISIPAQUE® formulations of the latter being well suited for injection into humans. As described under Materials and Methods, two fractions were collected, the full-particle fraction (lower band in the 40% phase) with an approximate density of 1.25 g/ml, and the empty-particle fraction (upper band in the 40% phase) with an approximate density of 1.23 g/ml. As shown in FIG. 5a, the mean titer of infectious particles in the full-particle fraction was $1.3 \times 10^{10}$ PFU/ml, while the GP and PP concentrations were respectively $9.2 \times 10^{12}$ GP/ml and $1.7 \times 10^{13}$ PP/ml. Titers in the empty-particle fraction were $6.3 \times 10^9$ PFU/ml, $4.6 \times 10^{12}$ GP/ml, and $3.9 \times 10^{13}$ PP/ml.

TABLE 2c

Empty particle fraction after VISIPAQUE ®/Ringer gradient centrifugation

| Titer[a] | empty particles fraction[b] |
|---|---|
| PP/ml | 3.9E+13 ± 2.9E+13 |
| GP/ml | 4.6E+12 ± 3.1E+12 |
| PFU/ml | 6.3E+09 ± 5.8E+09 |
| PP/PFU | 6.1E+03 ± 6.5E+03 |

Figure 5B:
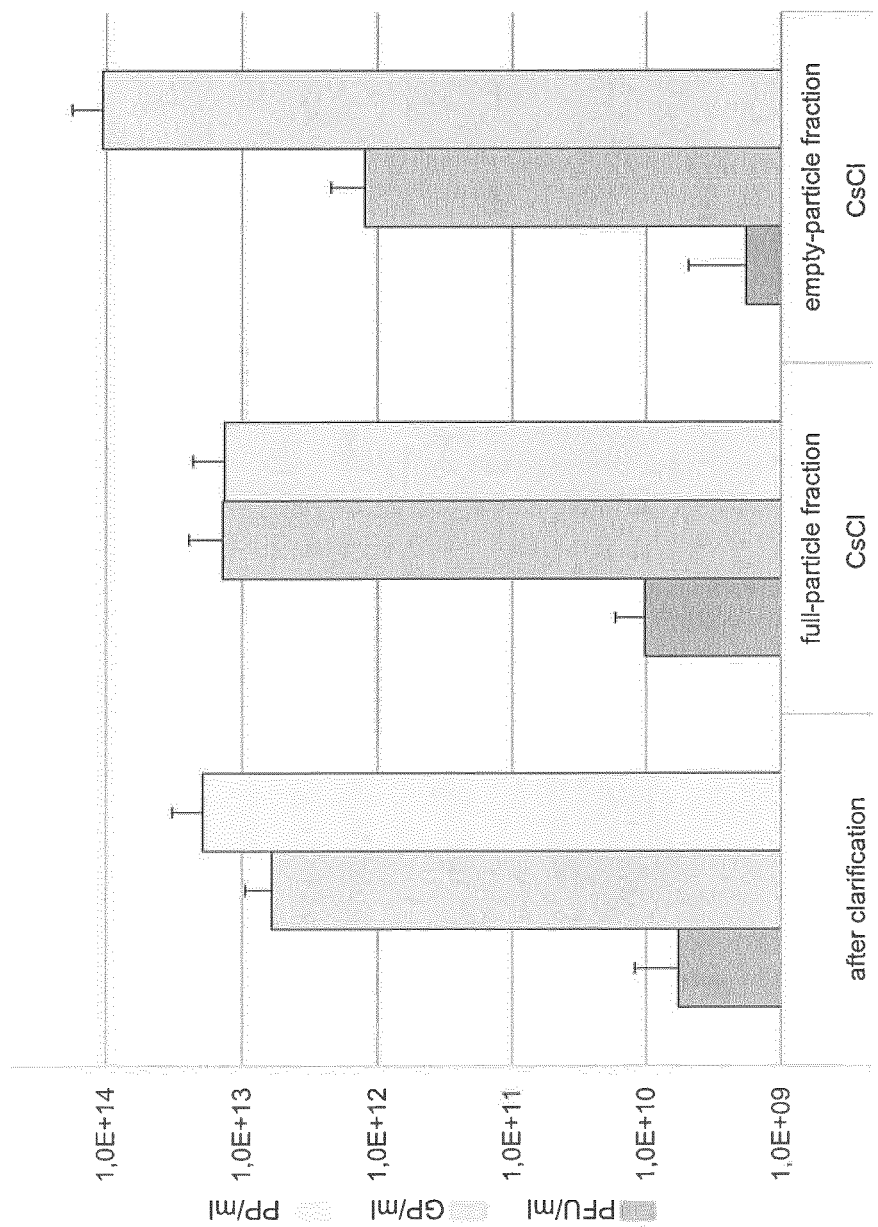

[a]PP, physical particles; GP, genome-containing particles; PFU, plaque-forming units
[b]After VISIPAQUE ®/Ringer gradient centrifugation As an alternative to obtain empty particles the second half of the virus harvest was fractionated on a continuous CsCl density gradient followed by dialysis against VTE. As shown in FIG. 5b, the empty-particle fraction displayed a slightly higher particle concentration ($1.1 \times 10^{14}$ PP/ml) and still contained residual infectious viruses ($1.8 \times 10^9$ PFU/ml, $1.2 \times 10^{12}$ GP/ml). The infectious particles in the full-particle fraction had a PFU titer comparable to that obtained after the IOD-PBS and VIS-Ringer gradient centrifugations ($1.0 \times 10^{10}$ PFU/ml), while contamination by empty particles was slightly reduced ($1.4 \times 10^{13}$ PP/ml). Both methods showed good reproducibility.

(C) Recovery of and Enrichment in Infectious H-1PV Particles

Figure 6A:
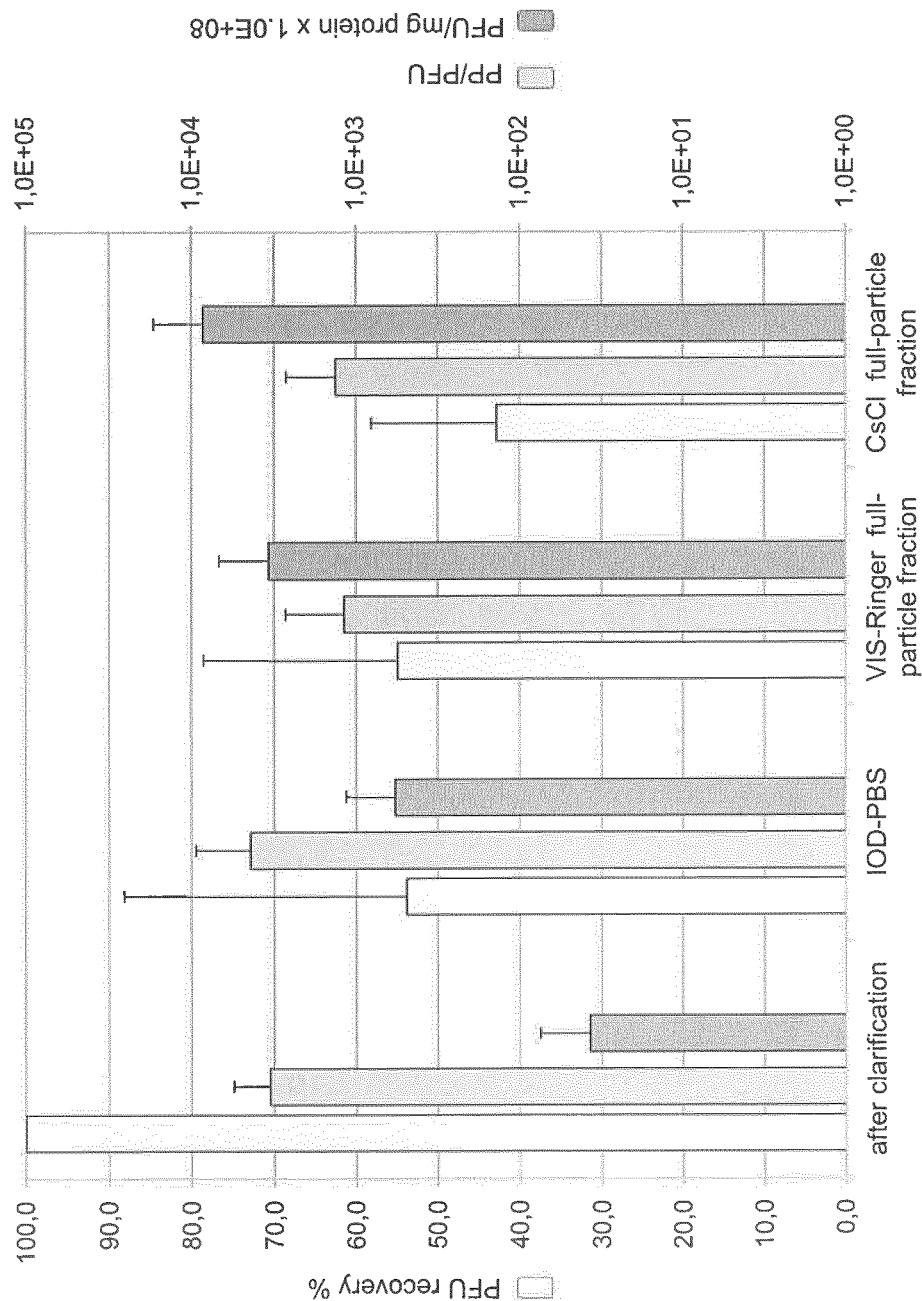

As shown in FIG. 6a, the IOD-PBS density gradient centrifugation led to a significant loss of infectious particles (46%). Further loss at the subsequent VIS-Ringer gradient step was negligible. It is noteworthy that the combined Iodixanol gradient centrifugations led to elimination of more than 90% of the total protein from the infectious virus fraction. The IOD-PBS step resulted in a 15.4-fold increase in specific activity and the VIS-Ringer step, in a further 5.9-fold increase. Hence, an overall 91-fold increase in specific activity, to $3 \times 10^{11}$ PFU/mg protein, was achieved through this purification process. On the other hand, CsCl density gradient purification led to a slightly higher loss of infectious particles (57%) but to more efficient protein elimination, resulting in a 227-fold increase in specific activity. The resulting particle-to-infectivity ratio (PP/PFU) was close to $10^3$:1 after both purification methods.

(D) Recovery of Empty Particles

Figure 6B:
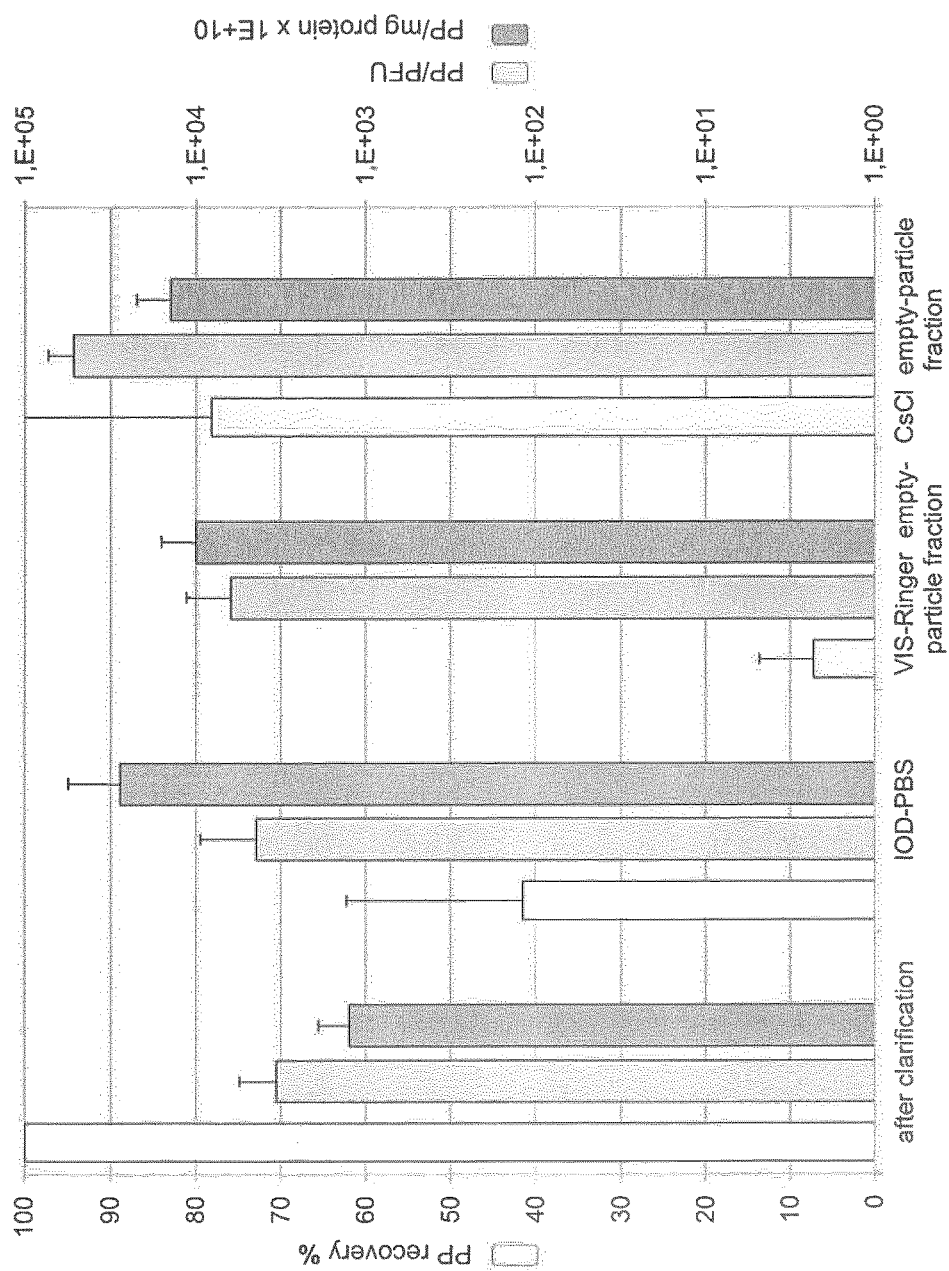

As shown in FIG. 6b, the recovery of physical particles in the empty-particle fraction was higher after CsCl density gradient purification (78% of the total PP from the clarified virus harvest) than after the IOD-PBS and VIS-Ringer density gradient centrifugations (7%). Furthermore, the VIS-Ringer empty-particle fraction contained a relatively high proportion of GPs (GP-to-PP ratio: 1:10) and PFU (PFU-to-PP ratio: $1:10^4$) as compared to the CsCl empty-particle fraction (GP-to-PP ratio: $1:10^2$; PFU-to-PP ratio: $1:10^5$). This leads us to recommend CsCl density gradient centrifugation for the preparation of empty capsids. The capsid concentration of the CsCl empty-particle fraction was about $1.4 \times 10^{14}$ PP/mg protein.

(E) H-1PV Concentration by Continuous VIS-Ringer Gradient Centrifugation

The titer of infectious particles in virus batches obtained by means of the above-mentioned IOD-PBS/VIS-Ringer and CsCl purification methods was about $1 \times 10^{10}$ PFU/ml. Since a higher titer is required for some applications, we tried replacing the VIS-Ringer step gradient with a continuous gradient. This enabled us to achieve a titer of $3 \times 10^{11}$ PFU/ml (FIG. 7).

EXAMPLE 6

Inactivated Empty Particles

In the empty-particle fraction obtained after CsCl fractionation, infectious virus could still be detected (PFU-to-PP ratio: $1:10^5$). To allow the use of empty particles as a non-infectious control, it was necessary to develop an inactivation method that eliminates virus infectivity without altering capsid structure. This was achieved by UV irradiation (Table 3). While UV irradiation did not change the PP titer, it reduced the measured GP titer by 90%. This is likely due to interference of the DNA damage induced in the viral genomes with their titration by Q-PCR. Importantly, UV irradiation reduced virus infectivity by more than 7 logs, with a residual infectivity as low as 1 PFU per $7 \times 10^{11}$ PP. This made it possible to use purified preparations of UV-irradiated empty particles as non-infectious controls in preclinical studies of the oncolytic effects of H-1PV (Kiprianova et al., 2011).

TABLE 3

Effect of UV irradiation on contamination of the empty-particle fraction by infectious virions

| Titer[a] | Empty-particle fraction[b] | UV-inactivated empty-particle fraction[c] |
|---|---|---|
| PP/ml | 1.1 ± 0.7E+14 | 1.1 ± 0.7E+14 |
| GP/ml | 1.2 ± 1.0E+12 | 9.0 ± 5.1E+10 |

TABLE 3-continued

Effect of UV irradiation on contamination of the empty-particle fraction by infectious virions

| Titer[a] | Empty-particle fraction[b] | UV-inactivated empty-particle fraction[c] |
|---|---|---|
| PFU/ml | 1.8 ± 3.0E+09 | 1.6 ± 0.8E+02 |
| PP/PFU | 4.6 ± 4.3E+05 | 6.9 ± 4.9E+11 |

[a]PP, physical particles; GP, genome-containing particles; PFU, plaque-forming units
[b]After CsCl gradient centrifugation (see FIG. 6b)
[c]254 nm, 0.5 mW/cm$^2$, samples irradiated 4 times for 2 min at 5-min intervals

EXAMPLE 7

Purity of the H-1PV Preparations

The H-1PV preparations were analyzed for protein and DNA contamination, the presence of endotoxins, and sterility. Proteins from different steps and gradient fractions in the purification process were analyzed by SDS-PAGE and revealed by silver staining. As illustrated in FIG. 8a, the expected viral polypeptides VP1, VP2, and VP3 were detected. The amounts of impurities remaining after density gradient fractionation were low to undetectable. The two purification methods were similarly effective. It is worth noting that the CsCl-purified empty particles were devoid of VP3, in keeping with the fact that empty capsids fail to undergo VP2-to-VP3 cleavage (Paradiso et al., 1984; Tattersall et al., 1976). No significant capsid protein degradation was observed after UV irradiation. Western blot analysis confirmed the identity of the VP polypeptide bands (FIG. 8b). No ultrastructural difference between non- and UV-irradiated capsids was observed by electron microscopy (FIG. 8c,d). Purified batches of full capsids contained less than 2.5 EU/ml, whatever the purification method, while empty, inactivated particle batches contained less than 25 EU/ml, compatible with the use of H-1PV preparations in animal models under the US food and drug administration limit of 5 EU/kg body weight (Malyala and Singh, 2008). All preparations proved to be sterile.

LIST OF REFERENCES

Angelova, A. L., Aprahamian, M., Balboni, G., Delecluse, H. J., Feederle, R., Kiprianova, I., Grekova, S. P., Galabov, A. S., Witzens-Harig, M., Ho, A. D., Rommelaere, J. and Raykov, Z., 2009a. Oncolytic rat parvovirus H-1PV, a candidate for the treatment of human lymphoma: In vitro and in vivo studies. Molecular therapy; The journal of the American Society of Gene Therapy 17, 1164-72.

Angelova, A. L., Aprahamian, M., Grekova, S. P., Hajri, A., Leuchs, B., Giese, N. A., Dinsart, C., Herrmann, A., Balboni, G., Rommelaere, J. and Raykov, Z., 2009b. Improvement of Gemcitabine-Based Therapy of Pancreatic Carcinoma by Means of Oncolytic Parvovirus H-1PV. Clinical Cancer Research 15, 511-519.

Burnett, E., Cotmore, S. F. and Tattersall, P., 2006. Segregation of a single outboard left-end origin is essential for the viability of parvovirus minute virus of mice. J Virol 80, 10879-83.

Cotmore, S. F., Agbandje-McKenna, M., Chiorini, J. A., Mukha, D. V., Pintel, D. J., Qiu, J., Soderlund-Venermo, M., Tattersall, P., Tijssen, P., Gatherer, D. and Davison, A. J., 2014. The family Parvoviridae. Archives of virology 159, 1239-47.

Dupressoir, T., Vanacker, J. M., Cornelis, J. J., Duponchel, N. and Rommelaere, J., 1989. Inhibition by parvovirus H-1 of the formation of tumors in nude mice and colonies in vitro by transformed human mammary epithelial cells. Cancer research 49, 3203-8.

Faisst, S., Faisst, S. R., Dupressoir, T., Plaza, S., Pujol, A., Jauniaux, J. C., Rhode, S. L. and Rommelaere, J., 1995. Isolation of a Fully Infectious Variant of Parvovirus H-1 Supplanting the Standard Strain in Human-Cells. Journal of Virology 69, 4538-4543.

Faisst, S., Guittard, D., Benner, A., Cesbron, J. Y., Schlehofer, J. R., Rommelaere, J. and Dupressoir, T., 1998. Dose-dependent regression of HeLa cell-derived tumours in SCID mice after parvovirus H-1 infection. International journal of cancer. Journal international du cancer 75, 584-9.

Faust, E. A. and Ward, D. C., 1979. Incomplete genomes of the parvovirus minute virus of mice: selective conservation of genome termini, including the origin for DNA replication. J Virol 32, 276-92.

Gao, K., Mengxin, L., Li, Z., Qin, S., Jia, L., Shaoyong, L., Ran, H., Yu, Z., Gregory, H., Junzhi, W. and Guangping, G., 2014. Empty virions in AAV8 vector preparations reduce transduction efficiency and may cause total viral particle dose-limiting side effects. Molecular Therapy—Methods & Clinical Development 1.

Geletneky, K., Huesing, J., Rommelaere, J., Schlehofer, J. R., Leuchs, B., Dahm, M., Krebs, O., von Knebel Doeberitz, M., Huber, B. and Hajda, J., 2012. Phase I/IIa study of intratumoral/intracerebral or intravenous/intracerebral administration of Parvovirus H-1 (ParvOryx) in patients with progressive primary or recurrent glioblastoma multiforme: ParvOryx01 protocol. BMC cancer 12, 99.

Geletneky, K., Kiprianova, I., Ayache, A., Koch, R., Herrero, Y. C. M., Deleu, L., Sommer, C., Thomas, N., Rommelaere, J. and Schlehofer, J. R., 2010. Regression of advanced rat and human gliomas by local or systemic treatment with oncolytic parvovirus H-1 in rat models. Neuro-oncology 12, 804-14.

Grekova, S. P., Aprahamian, M., Daeffler, L., Leuchs, B., Angelova, A., Giese, T., Galabov, A., Heller, A., Giese, N. A., Rommelaere, J. and Raykov, Z., 2011. Interferon gamma improves the vaccination potential of oncolytic parvovirus H-1PV for the treatment of peritoneal carcinomatosis in pancreatic cancer. Cancer biology & therapy 12, 888-95.

Griffith, O. M., 2006. Practical Techniques for centrifugal separations. FiberLite, Piramon Technologies, Inc.

Halder, S., Nam, H. J., Govindasamy, L., Vogel, M., Dinsart, C., Salome, N., McKenna, R. and Agbandje-McKenna, M., 2012. Production, purification, crystallization and structure determination of H-1 Parvovirus. Acta crystallographica. Section F, Structural biology and crystallization communications 68, 1571-6.

Hanson, N. D. and Rhode, S. L., 3rd, 1991. Parvovirus NS1 stimulates P4 expression by interaction with the terminal repeats and through DNA amplification. J Virol 65, 4325-33.

Hundt, B., Best, C., Schlawin, N., Kassner, H., Genzel, Y. and Reichl, U., 2007. Establishment of a mink enteritis vaccine production process in stirred-tank reactor and Wave Bioreactor microcarrier culture in 1-10 L scale. Vaccine 25, 3987-95.

Kestler, J., Neeb, B., Struyf, S., Van Damme, J., Cotmore, S. F., D'Abramo, A., Tattersall, P., Rommelaere, J., Dinsart, C. and Cornelis, J. J., 1999. cis requirements for the efficient production of recombinant DNA vectors based on autonomous parvoviruses. Human Gene Therapy 10, 1619-1632.

Kiprianova, I., Thomas, N., Ayache, A., Fischer, M., Leuchs, B., Klein, M., Rommelaere, J. and Schlehofer, J. R., 2011. Regression of Glioma in Rat Models by Intranasal Application of Parvovirus H-1. Clinical Cancer Research 17, 5333-5342.

Kongsvik, J. R. and Toolan, H. W., 1972. Effect of proteolytic enzymes on the hemagglutinating property of the parvoviruses, H-1, H-3, and RV. Proceedings of the Society for Experimental Biology and Medicine. Society for Experimental Biology and Medicine 140, 140-4.

Kuck, D., Kern, A. and Kleinschmidt, J. A., 2007. Development of AAV serotype-specific ELISAs using novel monoclonal antibodies. J Virol Methods 140, 17-24.

Lacroix, J., Leuchs, B., Li, J., Hristov, G., Deubzer, H. E., Kulozik, A. E., Rommelaere, J., Schlehofer, J. R. and Witt, O., 2010. Parvovirus H1 selectively induces cytotoxic effects on human neuroblastoma cells. International journal of cancer. Journal international du cancer 127, 1230-9.

Leuchs, B., Kern, A., Kuerschner, K., Mueller, M., Muenstermann, S. and Rommelaere, J. 2010. Antibody that binds to H-1 parvovirus, European Patent pp. 1-24.

Li, J., Bonifati, S., Hristov, G., Marttila, T., Valmary-Degano, S., Stanzel, S., Schnolzer, M., Mougin, C., Aprahamian, M., Grekova, S. P., Raykov, Z., Rommelaere, J. and Marchini, A., 2013. Synergistic combination of valproic acid and oncolytic parvovirus H-1PV as a potential therapy against cervical and pancreatic carcinomas. EMBO molecular medicine 5, 1537-55.

Malyala, P. and Singh, M., 2008. Endotoxin limits in formulations for preclinical research. Journal of pharmaceutical sciences 97, 2041-4.

Nuesch, J. P., Lacroix, J., Marchini, A. and Rommelaere, J., 2012. Molecular pathways: rodent parvoviruses—mechanisms of oncolysis and prospects for clinical cancer treatment. Clin Cancer Res 18, 3516-23.

Okada, T., Nonaka-Sarukawa, M., Uchibori, R., Kinoshita, K., Hayashita-Kinoh, H., Nitahara-Kasahara, Y., Takeda, S. and Ozawa, K., 2009. Scalable purification of adeno-associated virus serotype 1 (AAV1) and AAV8 vectors, using dual ion-exchange adsorptive membranes. Hum Gene Ther 20, 1013-21.

Paradiso, P. R., 1981. Infectious process of the parvovirus H-1: correlation of protein content, particle density, and viral infectivity. J Virol 39, 800-7.

Paradiso, P. R., Williams, K. R. and Costantino, R. L., 1984. Mapping of the amino terminus of the H-1 parvovirus major capsid protein. J Virol 52, 77-81.

Q6B. 1999. ICH HARMONISED TRIPARTITE GUIDELINE SPECIFICATIONS: TEST PROCEDURES AND ACCEPTANCE CRITERIA FOR BIOTECHNOLOGICAL/BIOLOGICAL PRODUCTS Q6B ICH Expert Working Group.

Qu, G., Bahr-Davidson, J., Prado, J., Tai, A., Cataniag, F., McDonnell, J., Zhou, J., Hauck, B., Luna, J., Sommer, J. M., Smith, P., Zhou, S., Colosi, P., High, K. A., Pierce, G. F. and Wright, J. F., 2007. Separation of adeno-associated virus type 2 empty particles from genome containing vectors by anion-exchange column chromatography. J Virol Methods 140, 183-92.

Rajendran, R., Lingala, R., Vuppu, S. K., Bandi, B. O., Manickam, E., Macherla, S. R., Dubois, S., Havelange, N. and Maithal, K., 2014. Assessment of packed bed bioreactor systems in the production of viral vaccines. AMB Express 4, 25.

Rommelaere, J., Geletneky, K., Angelova, A. L., Daeffler, L., Dinsart, C., Kiprianova, I., Schlehofer, J. R. and Raykov, Z., 2010. Oncolytic parvoviruses as cancer therapeutics. Cytokine & growth factor reviews 21, 185-95.

Tattersall, P. and Bratton, J., 1983. Reciprocal productive and restrictive virus-cell interactions of immunosuppressive and prototype strains of minute virus of mice. J Virol 46, 944-55.

Tattersall, P., Cawte, P. J., Shatkin, A. J. and Ward, D. C., 1976. Three structural polypeptides coded for by minite virus of mice, a parvovirus. J Virol 20, 273-89.

Toolan, H. W., Dalldore, G., Barclay, M., Chandra, S. and Moore, A. E., 1960. An Unidentified, Filtrable Agent Isolated from Transplanted Human Tumors. Proceedings of the National Academy of Sciences of the United States of America 46, 1256-8.

Tuynder, M., Fiucci, G., Prieur, S., Lespagnol, A., Géant, A., Beaucourt, S., Duflaut, D., Besse, S., Susini, L., Cavarelli, J., Moras, D., Amson, R., Telerman, A.,2004, Translationally controlled tumor protein is a target of tumor reversion, PNAS, Vol. 101, No. 43, pp. 15364-15369

Weaver, J., Husson, S. M., Murphy, L. and Wickramasinghe, S. R., 2013. Anion exchange membrane adsorbers for flow-through polishing steps: Part II. Virus, host cell protein, DNA clearance, and antibody recovery. Biotechnology and bioengineering 110, 500-10.

Weiss, N., Stroh-Dege, A., Rommelaere, J., Dinsart, C. and Salome, N., 2012. An in-frame deletion in the NS protein-coding sequence of parvovirus H-1PV efficiently stimulates export and infectivity of progeny virions. J Virol 86, 7554-64.

Wobus, C. E., Hugle-Dorr, B., Girod, A., Petersen, G., Hallek, M. and Kleinschmidt, J. A., 2000. Monoclonal antibodies against the adeno-associated virus type 2 (AAV-2) capsid: epitope mapping and identification of capsid domains involved in AAV-2-cell interaction and neutralization of AAV-2 infection. J Virol 74, 9281-93.

Zolotukhin, S., Byrne, B. J., Mason, E., Zolotukhin, I., Potter, M., Chesnut, K., Summerford, C., Samulski, R. J. and Muzyczka, N., 1999. Recombinant adeno-associated virus purification using novel methods improves infectious titer and yield. Gene Ther 6, 973-85.

The invention claimed is:

1. A method for producing empty inactive or full active parvovirus particles, wherein the parvovirus is H-1PV, said method comprising:
    (a) providing the producer cell line NB-324K;
    (b) growing the cell line under suitable conditions and infecting the cells at a cell density from 2.0 to $5.0 \times 10^4$ cells/cm$^2$ with the parvovirus at a MOI of 0.5 to $2 \times 10^2$ PFU/cells;
    (c) harvesting the cells 2 to 6 days post-infection and obtaining a cell pellet by centrifugation;
    (d) subjecting the resuspended cell pellet to a mechanical, physical or chemical cell lysis method for obtaining a parvovirus containing cell lysate;
    (e) sonicating the cell lysate and subjecting it to DNAse treatment;
    (f) clarifying the DNAse-treated parvovirus harvest by filtration; and
    (g1) purifying the parvovirus by two successive density gradient ultracentrifugations, wherein the first gradient is a Iodixanol/PBS step gradient and the second gradient is a Iodixanol/Ringer step gradient or a Iodixanol/

Ringer continuous gradient for obtaining full active parvovirus particles in one fraction and empty parvovirus particles in another fraction.

2. The method of claim 1, wherein the cell density of step (b) is from 3.0 to $4.0 \times 10^4$ cells/cm$^2$.

3. The method of claim 1, wherein for step (f) a 0.2-µm filter with prefilter is used.

4. The method of claim 1, wherein the producer cell line NB-324K is characterized by
 (a) a viability of at least 95%;
 (b) a passage number below 20; and/or
 (c) lack of mycoplasma contamination.

5. The method of claim 1, wherein virus production is performed in a collection system.

6. The method of claim 5, wherein the collection system is a 10-layer cell culture chamber.

7. The method of claim 1 further comprising determining the ratio of native parvovirus capsids to non-assembled capsid proteins or denatured capsids.

8. The method of claim 7, wherein the ratio is determined by using a monoclonal antibody.

9. The method of claim 8, wherein the monoclonal antibody is the antibody BL-H1 (DSM ACC 3030).

* * * * *